United States Patent
Kagami

(10) Patent No.: US 10,321,683 B2
(45) Date of Patent: Jun. 18, 2019

(54) INSECTICIDAL, MITICIDAL, NEMATICIDAL, MOLLUSCICIDAL, MICROBICIDAL, OR BACTERICIDAL COMPOSITION AND METHOD FOR CONTROLLING PEST

(71) Applicant: NISSAN CHEMICAL INDUSTRIES, LTD., Tokyo (JP)

(72) Inventor: Takahiro Kagami, Shiraoka (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 18 days.

(21) Appl. No.: 15/322,286

(22) PCT Filed: Jun. 30, 2015

(86) PCT No.: PCT/JP2015/068850
§ 371 (c)(1),
(2) Date: Dec. 27, 2016

(87) PCT Pub. No.: WO2016/002790
PCT Pub. Date: Jan. 7, 2016

(65) Prior Publication Data
US 2017/0135347 A1    May 18, 2017

(30) Foreign Application Priority Data
Jun. 30, 2014 (JP) ................. 2014-134037

(51) Int. Cl.
| A01N 43/80 | (2006.01) |
| A01N 41/10 | (2006.01) |
| A01N 37/34 | (2006.01) |
| A01N 37/08 | (2006.01) |
| A01N 43/22 | (2006.01) |
| A01N 47/30 | (2006.01) |
| A01N 47/06 | (2006.01) |
| A01N 43/56 | (2006.01) |
| A01N 43/713 | (2006.01) |

(52) U.S. Cl.
CPC ............. *A01N 43/80* (2013.01); *A01N 37/08* (2013.01); *A01N 37/34* (2013.01); *A01N 41/10* (2013.01); *A01N 43/22* (2013.01); *A01N 43/56* (2013.01); *A01N 43/713* (2013.01); *A01N 47/06* (2013.01); *A01N 47/30* (2013.01)

(58) Field of Classification Search
CPC ........ A01N 43/80; A01N 37/08; A01N 37/34; A01N 41/10; A01N 43/22; A01N 43/56; A01N 43/713; A01N 47/06; A01N 47/30
USPC ........................................................ 514/341
See application file for complete search history.

(56) References Cited

U.S. PATENT DOCUMENTS

2013/0210623 A1* 8/2013 Cassayre ................ A01N 43/80
504/100

FOREIGN PATENT DOCUMENTS

| JP | 2009-108046 A | 5/2009 |
| JP | 2011-527306 A | 10/2011 |
| JP | 2011-527307 A | 10/2011 |
| JP | 2012-153620 A | 8/2012 |
| JP | 2012-153621 A | 8/2012 |
| JP | 2014-114246 A | 6/2014 |
| WO | 2005/085216 A1 | 9/2005 |
| WO | 2007/026965 A1 | 3/2007 |
| WO | 2010/003877 A1 | 1/2010 |
| WO | 2010/003923 A1 | 1/2010 |
| WO | 2011/154433 A2 | 12/2011 |
| WO | 2011/154434 A2 | 12/2011 |

OTHER PUBLICATIONS

MacBean, C., "A World Compendium the Pesticide Manual Sixteenth Edition," Supplementary Entries—Extended, 2012, pp. 1-557.
Sep. 8, 2015 Written Opinion issued in International Patent Application No. PCT/JP2015/068850.
Sep. 8, 2015 International Search Report issued in International Patent Application No. PCT/JP2015/068850.
Oct. 31, 2018 Office Action Issued in Chinese Patent Application No. 201580035023.9.
Feb. 5, 2019 Office Action Issued in Israeli Patent Application No. 249797.
Feb. 14, 2019 Office Action Issued in Indian Patent Application No. 201717000213.
Mar. 13, 2019 Office Action Issued in Ukrainian Patent Application No. a 2017 00741.

* cited by examiner

*Primary Examiner* — Kristin A Vajda
(74) *Attorney, Agent, or Firm* — Oliff PLC

(57) ABSTRACT

The present invention provides a novel insecticidal, miticidal, nematicidal, microbicidal, or bactericidal composition and a novel pest control method. An insecticide, miticide, nematicide, molluscicide, disinfectant, or bactericide composition containing one or two substances selected from 4-[5-(3,5-dichlorophenyl)-4,5-dihydro-5-(trifluoromethyl) isoxazole-3-yl]-2-methyl-N-[2-oxo-2-[(2,2,2-trifluoroethyl) amino]ethyl]benzamide or (Z)-4-[5-(3,5-dichlorophenyl)-5-trifluoromethyl-4,5-dihydroisoxazole-3-yl]-N-(methoxyiminomethyl)-2-methylbenzamide, and one or more substances selected from known insecticide, miticide, nematicide, molluscicide, disinfectant, or bactericide compounds.

2 Claims, No Drawings

INSECTICIDAL, MITICIDAL, NEMATICIDAL, MOLLUSCICIDAL, MICROBICIDAL, OR BACTERICIDAL COMPOSITION AND METHOD FOR CONTROLLING PEST

TECHNICAL FIELD

The present invention relates to a pesticide characterized by mixing an isoxazoline-substituted benzamide compound or a salt thereof and an active ingredient compound of known insecticides, miticides, nematicides, molluscicides, microbicides, or bactericides.

BACKGROUND ART

First active ingredient compounds of a composition of the present invention, that is, 4-[5-(3,5-dichlorophenyl)-4,5-dihydro-5-(trifluoromethyl)isoxazole-3-yl]-2-methyl-N-[2-oxo-2-[(2,2,2-trifluoroethyl)amino]ethyl]benzamide and (Z)-4-[5-(3,5-dichlorophenyl)-5-trifluoromethyl-4,5-dihydroisoxazole-3-yl]-N-(methoxyiminomethyl)-2-methylbenzamide, have been known as isoxazoline-substituted benzamide compounds having activities as pesticides (see, for example, Patent Documents 1 and 2).

Also, compounds described as active ingredient groups A to R having insecticidal activities, miticidal activities, nematicidal activities, molluscicidal activities, microbicidal activities, or bactericidal activities are second active ingredient compounds of the composition of the present invention (hereinafter, abbreviated as "second active ingredient compounds II"), and all of them are well-known (see, for example, Non-Patent Document 1).

In addition, compositions containing the first active ingredient compound of the present invention, that is, 4-[5-(3,5-dichlorophenyl)-4,5-dihydro-5-(trifluoromethyl)isoxazole-3-yl]-2-methyl-N-[2-oxo-2-[(2,2,2-trifluoroethyl)amino] ethyl]benzamide or (Z)-4-[5-(3,5-dichlorophenyl)-5-trifluoromethyl-4,5-dihydroisoxazole-3-yl]-N-(methoxyiminomethyl)-2-methylbenzamide and known insecticides, miticides, nematicides, molluscicides, microbicides, or bactericides, have also been known (see, for example, Patent Documents 3, 4, and 5).

PRIOR ART DOCUMENTS

Patent Documents

Patent Document 1: WO2005/085216
Patent Document 2: WO2007/026965
Patent Document 3: Japanese Patent Application Publication No. 2009-108046 (JP 2009-108046 A)
Patent Document 4: Japanese Patent Application Publication No. 2012-153620 (JP 2012-153620 A)
Patent Document 5: Japanese Patent Application Publication No. 2012-153621 (JP 2012-153621 A)

Non-Patent Documents

Non-Patent Document 1: The Pesticide Manual 16th Edition, The British Crop Protection Council, 2012

SUMMARY OF THE INVENTION

Problem to be Solved by the Invention

Nowadays, insecticides, miticides, and microbicides are developed for controlling various pests, such as horticulture pests, forest pests, and sanitary pests, and a variety of such chemicals are prepared for actual uses. However, by using these chemicals for long years, pests have acquired insecticide resistances, and pathogens have acquired microbicide resistances. Accordingly, the cases that are hard to be controlled by conventional chemicals have been increasing in recent years. Also, some of such chemicals are highly toxic, and gradually disturbing ecosystems by remaining in environments for long years. Accordingly, developments of novel chemicals that are low toxic and low persistent, in addition to having excellent pest control effects, have always been expected.

Meanwhile, when taking into account the biological diversities of insects and pathogens, and varieties of their modes and situations of infliction, efficient control of all pests in all situations is difficult by uses of only one type of such novel chemicals or conventional known chemicals. Accordingly, novel methods, in which a plurality of insecticides, miticides, nematicides, molluscicides, microbicides, or bactericides are suitably combined so that higher control effects can be induced, have been strongly demanded in order to control harmful organisms that are difficult to control.

Means for Solving the Problem

In view of above situations, and as results of intensive studies to develop pesticides that show excellent pest control activities, and show little adverse impact to mammals, fishes, and non-target organisms such as natural enemies and beneficial insects, the present inventors found that a composition that contains an isoxazoline-substituted benzamide compound and some known compounds having insecticidal, miticidal, nematicidal, molluscicidal, microbicidal, or bactericidal activities exhibits excellent insecticidal, miticidal, nematicidal, molluscicidal, microbicidal, or bactericidal effects synergistically, which could not be expected from single uses of them, whereby the present invention was completed.

That is, the present invention relates to compositions of [1] to [6](hereinafter, referred to as compositions of the present invention), and control methods of [7] to [8] (hereinafter, referred to as methods of the present invention) described in below.

[1]

An insecticidal, miticidal, nematicidal, molluscicidal, microbicidal, or bactericidal composition comprising at least two types of active compounds with amounts that are synergistically active, in which the two types of active compounds include:

1) one or two active compound(s) I containing 4-[5-(3,5-dichlorophenyl)-4,5-dihydro-5-(trifluoromethyl)isoxazole-3-yl]-2-methyl-N-[2-oxo-2-[(2,2,2-trifluoroethyl)amino] ethyl]benzamide or (Z)-4-[5-(3,5-dichlorophenyl)-5-trifluoromethyl-4,5-dihydroisoxazole-3-yl]-N-(methoxyiminomethyl)-2-methylbenzamide; and 2) one or more active compound(s) II selected from active ingredient groups A to R below.

Active ingredient group A (inhibitors of nucleic acid biosyntheses): benalaxyl, benalaxyl-M, furalaxyl, metalaxyl, metalaxyl-M, ofurace, oxadixyl, bupirimate, ethirimol, and hymexazol.

Active ingredient group B (inhibitors of mitoses and cell divisions): benomyl, carbendazim, fuberidazole, thiabendazole, thiophanate-methyl, diethofencarb, ethaboxam, zoxamide, pencycuron, and fluopicolide.

Active ingredient group C (inhibitors of respiration): diflumetorim, benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, thifluzamide, azoxystrobin, coumoxystrobin, dimoxystrobin, enestrobin, enoxastrobin, famoxadone, fenamidone, fenaminstrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, pyribencarb-methyl, pyriminostrobin, triclopyricab, trifloxystrobin, amisulbrom, cyazofamid, dinocap, fluazinam, meptyldinocap, fentin, tributyltin oxide, silthiofam, and ametoctradin.

Active ingredient group D (inhibitors of amino acid biosyntheses and protein biosyntheses): cyprodinil, mepanipyrim, pyrimethanil, blasticidin-S, and kasugamycin.

Active ingredient group E (chemicals affecting signal transduction systems): proquinazid, quinoxyfen, fenpiclonil, fludioxonil, chlozolinate, iprodione, procymidone, and vinclozolin.

Active ingredient group F (inhibitors of lipid syntheses and cell membrane syntheses): edifenphos, iprobenfos, isoprothiolane, pyrazophos, biphenyl, chloroneb, dicloran, etridiazole, quintozene, tecnazene, tolclofos-methyl, propamocarb hydrochloride, and *Bacillus subtilis* (Strain: D747, FZB24, GBO3, HAI0404, MBI600, QST713, Y1336, and the like).

Active ingredient group G (inhibitors of sterol biosyntheses): azaconazole, bitertanol, bromuconazole, climbazole, cyproconazole, diclobutrazol, difenoconazole, diniconazole, diniconazole-M, epoxiconazole, etaconazole, fenarimol, fenbuconazole, fluotrimazole, fluquinconazole, flusilazole, flutriafol, furconazole, hexaconazole, imazalil, imibenconazole, ipconazole, metconazole, myclobutanil, nuarimol, oxpoconazole fumarate, pefurazoate, penconazole, prochloraz, propiconazole, prothioconazole, pyrifenox, pyrisoxazole, simeconazole, tebuconazole, tetraconazole, triadimefon, triadimenol, triflumizole, triforine, triticonazole, aldimorph, dodemorph-acetate, fenpropidin, fenpropimorph, piperalin, spiroxamine, tridemorph, fenhexamid, and fenpyrazamine.

Active ingredient group H (inhibitors of cell wall syntheses): validamycin, polyoxins, polyoxin-D (polyoxorim), benthiavalicarb-isopropyl, dimethomorph, flumorph, iprovalicarb, mandipropamid, pyrimorph, and valifenalate.

Active ingredient group I (inhibitors of melanin syntheses): phthalide, pyroquilon, tricyclazole, carpropamid, diclocymet, and fenoxanil.

Active ingredient group J (chemicals inducing host defense): acibenzolar-S-methyl, probenazole, isotianil, tiadinil, and laminarin.

Active ingredient group K (multifunctional chemicals): bordeaux mixture, cheshunt mixture, basic copper carbonate, copper hydroxide, copper naphthenate, copper oleate, copper oxychloride, copper sulfate, basic copper sulfate, oxine copper, calcium polysulfide, sulfur, amobam, ferbam, mancozeb, maneb, metiram, polycarbamate, propineb, thiram, ziram, captan, folpet, chlorothalonil, dichlofluanid, tolylfluanid, guazatine, iminoctadine-albesilate, iminoctadine-triacetate, anilazine, dithianon, chinomethionat, and fluoroimide.

Active ingredient group L (other chemicals): cyflufenamid, cymoxanil, diclomezine, dodine, ferimzone, flusulfamide, flutianil, fosetyl-aluminium, metrafenone, oxathiapiprolin, picarbutrazox, pyriofenone, tebufloquin, tolprocarb, triazoxide, potassium hydrogen carbonate, sodium hydrogen carbonate, Chinese mushroom mycelium extract, Chinese mushroom carpophore extract, BCF-082 (test name), NNF-0721 (test name), and ZF-9646 (test name).

Active ingredient group M (insecticides): abamectin, acephate, acetamiprid, afidopyropen, afoxolaner, alanycarb, aldicarb, allethrin, azamethiphos, azinphos-ethyl, azinphos-methyl, *Bacillus thuringiensis*, bendiocarb, benfluthrin, benfuracarb, bensultap, bifenthrin, bioallethrin, bioresmethrin, bistrifluron, buprofezin, butocarboxim, carbaryl, carbofuran, carbosulfan, cartap, chlorantraniliprole, chlorethoxyfos, chlorfenapyr, chlorfenvinphos, chlorfluazuron, chlormephos, chlorpyrifos, chlorpyrifos-methyl, chromafenozide, clothianidin, cyanophos, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, beta-cypermethrin, zeta-cypermethrin, cyphenothrin, cyromazine, deltamethrin, diafenthiuron, diazinon, dichlorvos, diflubenzuron, dimethoate, dimethylvinphos, dinotefuran, diofenolan, disulfoton, emamectin-benzoate, empenthrin, endosulfan, alpha-endosulfan, EPN, esfenvalerate, ethiofencarb, ethiprole, etofenprox, etrimfos, fenitrothion, fenobucarb, fenoxycarb, fenthion, fenvalerate, fipronil, flometoquin, flonicamid, fluazuron, flubendiamide, flucycloxuron, flucythrinate, flufenerim, flufenoxuron, flufiprole, fluhexafon, flumethrin, flupyradifurone, fluvalinate, tau-fluvalinate, fonofos, furathiocarb, halofenozide, heptafluthrin, hexaflumuron, hydramethylnon, imidacloprid, imiprothrin, indoxacarb, indoxacarb-MP, isoprocarb, isoxathion, lepimectin, lufenuron, malathion, meperfluthrin, metaflumizone, metaldehyde, methacrifos, methamidophos, methidathion, methomyl, methoprene, methoxychlor, methoxyfenozide, metofluthrin, muscalure, nitenpyram, novaluron, noviflumuron, omethoate, oxydemeton-methyl, parathion-methyl, permethrin, phenothrin, phenthoate, phorate, phosalone, phosmet, phoxim, pirimicarb, pirimiphos-methyl, profenofos, prothiofos, pymetrozine, pyraclofos, pyrethrins, pyridalyl, pyrifluquinazon, pyriprole, pyriproxyfen, resmethrin, rotenone, silafluofen, spinetoram, spinosad, spirotetramat, sulfotep, sulfoxaflor, tebufenozide, teflubenzuron, tefluthrin, terbufos, tetrachlorvinphos, tetramethrin, d-tetramethrin, tetramethylfluthrin, tetraniliprole, thiacloprid, thiamethoxam, thiocyclam, thiodicarb, thiofanox, thiometon, tolfenpyrad, tralomethrin, transfluthrin, triazamate, trichlorfon, triflumezopyrim, triflumuron, ME5382 (test name), MIE-1209 (test name), and ZDI2501 (test name).

Active ingredient group N (miticides): acequinocyl, acrinathrin, amidoflumet, amitraz, azocyclotin, benzoximate, bifenazate, bromopropylate, clofentezine, cyenopyrafen, cyflumetofen, dicofol, dienochlor, etoxazole, fenazaquin, fenbutatin oxide, fenothiocarb, fenpropathrin, fenpyroximate, fluacrypyrim, formetanate, halfenprox, hexythiazox, milbemectin, propargite, pyflubumide, pyridaben, pyrimidifen, spirodiclofen, spiromesifen, tebufenpyrad, and NA-89 (test name).

Active ingredient group O (nematicides): cadusafos, dichlofenthion, ethoprophos, fenamiphos, fluensulfone, fosthiazate, fosthietan, imicyafos, isamidofos, isazofos, methyl bromide, methyl isothiocyanate, oxamyl, sodium azide, thiaxafen, BYI-1921 (test name), and MAI-08015 (test name).

Active ingredient group P (insect removing chemicals): acriflavine, albendazole, atovaguone, azithromycin, bithionol, bromofenofos, cambendazole, carnidazole, chloroquine, clazuril, clindamycin hydrochloride, clorsulon, closantel, coumaphos, cymiazol, dichlorophen, diethylcarbamazine, diminazene, disophenol, dithiazanine iodide, doxycycline hydrochloride, doramectin, emodepside, eprinomectin, febantel, fenbendazole, flubendazole, furazolidone, glycalpyramide, imidocarb, ivermectin, levamisole, mebendazole, mefloquine, melarsamine hydrochloride, metronidazole, metyridine, milbemycin oxime, monepantel, morantel tartrate, moxidectin, nicarbazin, niclosamide, nitroscanate, nitroxynil, omphalotin, oxantel pamoate, oxantel tartrate, oxfendazolee, oxibendazole, oxyclozanide, pamaquine, phenothiazine, piperazine adipate, piperazine citrate, piperazine phosphate, PNU-97333 (paraherquamide A), PNU-141962 (2-deoxyparaherquamide), praziquantel, primaquine, propetamphos, propoxur, pyrantel pamoate, pyrimethamine, santonin, selamectin, sulfadimethoxine, sulfadoxine, sulfamerazine, sulfamonomethoxine, sulfamoildapsone, thiabendazole, tinidazole, toltrazuril, tribromsalan, and triclabendazole.

Active ingredient group Q (antifungal agents): ketoconazole and miconazole nitrate.

Active ingredient group R (antimicrobial agents): amoxicillin, ampicillin, bethoxazin, bithionol, bronopol, cefapirin, cefazolin, cefquinome, ceftiofur, chlortetracycline, clavulanic acid, danofloxacin, difloxacin, dinitolmide, enrofloxacin, florfenicol, lincomycin, lomefloxacin, marbofloxacin, miloxacin, mirosamycin, nitrapyrin, norfloxacin, octhilinone, ofloxacin, orbifloxacin, oxolinic acid, oxytetracycline, penicillin, streptomycin, thiamphenicol, tiamulin fumarate, tilmicosin phosphate, acetylisovaleryltylosin, tylosin phosphate, tulathromycin, valnemulin, calcinated shell calcium (calcium oxide), genus *Talaromyces*, genus *Trichoderma*, and genus *Coniothyrium*.

[2]
The insecticidal, miticidal, nematicidal, microbicidal, or bactericidal composition according to [1], comprising the active compound II selected from the active ingredients M.

[3]
The insecticidal, miticidal, nematicidal, microbicidal, or bactericidal composition according to [2], comprising the active compound II selected from the active ingredient group M consisting of chlorantraniliprole, cyantraniliprole, flubendiamide, gamma-cyhalothrin, cyclaniliprole, tetraniliprole, spinosad, spinetoram, metaflumizone, flupyradifurone, flometoquin, bifenthrin, and flufenoxuron.

[4]
The insecticidal, miticidal, nematicidal, microbicidal, or bactericidal composition according to [3], comprising the active compound II selected from the active ingredient group M consisting of chlorantraniliprole, cyantraniliprole, flubendiamide, and gamma-cyhalothrin.

[5]
The insecticidal, miticidal, nematicidal, microbicidal, or bactericidal composition according to any one of [1] to [4], in which the active compound I is 4-[5-(3,5-dichlorophenyl)-4,5-dihydro-5-(trifluoromethyl)isoxazole-3-yl]-2-methyl-N-[2-oxo-2-[(2,2,2-trifluoroethyl)amino]ethyl]benzamide.

[6]
The insecticidal, miticidal, nematicidal, microbicidal, or bactericidal composition according to any one of [1] to [4], in which the active compound I is (Z)-4-[5-(3,5-dichlorophenyl)-5-trifluoromethyl-4,5-dihydroisoxazole-3-yl]-N-(methoxyiminomethyl)-2-methylbenzamide.

[7]
A method for controlling pests and diseases characterized in that a treatment is conducted with the one or two active compound(s) I as described in [1] and the one or more active compound(s) II as described in [1] at the same time or at different times that are close to each other.

[8]
A method for controlling pests characterized in that a treatment is conducted with the one or more active compound(s) I as described in [1] and the one or more active compound(s) II as described in [3] at the same time or at different times that are close to each other.

[9]
A chemical for controlling a pest parasitic to honey bees comprising at least one of 4-[5-(3,5-dichlorophenyl)-4,5-dihydro-5-(trifluoromethyl)isoxazole-3-yl]-2-methyl-N-[2-oxo-2-[(2,2,2-trifluoroethyl)amino]ethyl]benzamide, (Z)-4-[5-(3,5-dichlorophenyl)-5-trifluoromethyl-4,5-dihydroisoxazole-3-yl]-N-(methoxyiminomethyl)-2-methylbenzamide, and salts thereof.

[10]
The chemical for controlling a pest parasitic to honey bees according to [9], in which the pest parasitic to honey bees is *Varroa* mite, *Tropilaelaps clareae*, or *Acarapis woodi*.

[11]
The chemical for controlling a pest parasitic to honey bees according to [10], in which the pest parasitic to honey bees is *Varroa* mite.

[12]
A method for controlling the pest parasitic to honey bees, in which the chemical for controlling the pest parasitic to honey bees according to [9] is used.

Effects of the Invention

The composition of the present invention and the method of the present invention provide excellent synergistic control effects to a variety of pests, and provide sufficient synergistic control effects also to pests acquired resistances to conventional pesticides. Accordingly, the present invention can provide a useful novel pesticide composition and an effective control method using the composition.

MODES FOR CARRYING OUT THE INVENTION

One of the first active ingredients of the composition of the present invention is 4-[5-(3,5-dichlorophenyl)-4,5-dihydro-5-(trifluoromethyl)isoxazole-3-yl]-2-methyl-N-[2-oxo-2-[(2,2,2-trifluoroethyl)amino]ethyl]benzamide [hereinafter, referred to as Compound (1)] that is known as an isoxazoline-substituted benzamide compound. This is a well-known compound, and is described in WO2005/085216.

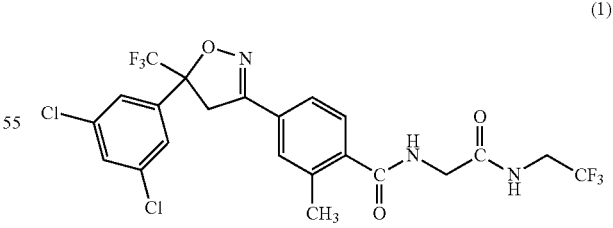

(1)

The other one of the first active ingredients of the composition of the present invention is (Z)-4-[5-(3,5-dichlorophenyl)-5-trifluoromethyl-4,5-dihydroisoxazole-3-yl]-N-(methoxyiminomethyl)-2-methylbenzamide [hereinafter, referred to as Compound (2)] that is known as an isoxazoline-substituted benzamide compound. This is a well-known compound, and is described in WO2007/026965.

(2)

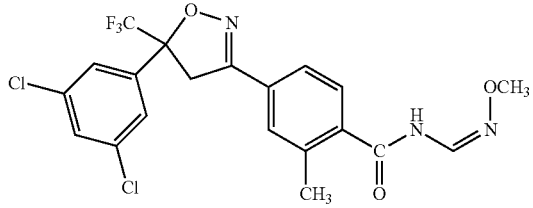

The first active ingredient compounds of the composition of the present invention, Compound (1) and Compound (2), have optically active substances caused by one asymmetric carbon atom existing on an isoxazoline ring, and the optically active substances may encompass racemates or optically active substances having any enantiomeric excesses.

Also, the first active ingredient compound of the composition of the present invention, Compound (2), may encompass a mixture of geometric isomers containing E-bodies with any percentages.

Among the first active ingredient compounds in the present invention, that is, among Compounds (1) and Compounds (2), (hereinafter, abbreviated as the "first active ingredient compounds I"), examples of a compound that can become an acid addition salt by a conventional procedure include a salt of a hydrohalic acid, such as hydrofluoric acid, hydrochloric acid, hydrobromic acid, and hydroiodic acid; a salt of an inorganic acid, such as nitric acid, sulfuric acid, phosphoric acid, chloric acid, and perchloric acid; a salt of a sulfonic acid, such as methanesulfonic acid, ethanesulfonic acid, trifluoromethanesulfonic acid, benzenesulfonic acid, and p-toluenesulfonic acid; a salt of a carboxylic acid, such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, and citric acid; and a salt of amino acid, such as glutamic acid and aspartic acid.

Among the first active ingredient compounds I in the present invention, examples of a compound that can become a metal salt by a conventional procedure include a salt of an alkali metal, such as lithium, sodium, and potassium; a salt of an alkaline earth metal, such as calcium, barium, and magnesium; and a salt of aluminum.

The second active ingredient compounds II of the composition of the present invention are well-known as insecticidal, miticidal, nematicidal, molluscicidal, microbicidal, or bactericidal compounds, and specific examples thereof are shown in Table 1 with the compound symbols. The first active ingredient compound I in the present invention, that is, each of Compound (1) and Compound (2) can be used in combination with each of the second active ingredient compounds II shown in Table 1. Specific examples of the combination include "Compound (1)+Compound (a)" and "Compound (2)+Compound (gy)." Due to appearances of resistant pests or resistant microbes, and due to lack of insecticidal or microbicidal spectra and residual activities in these compounds, spraying amounts and spraying frequencies of the chemicals tend to be increased, which in turn increases risk to humans, animals, and aquatic organisms. Thus, improvements in some of these compounds are required not only for control effects, but also for environmental safety.

TABLE 1

| No. | Compound Name (Common Name) |
|---|---|
| a | abamectin |
| b | acephate |
| c | acetamiprid |
| d | afidopyropen |
| e | afoxolaner |
| f | alanycarb |
| g | aldicarb |
| h | allethrin |
| i | azamethiphos |
| j | azinphos-ethyl |
| k | azinphos-methyl |
| l | bacillus thuringiensis |
| m | bendiocarb |
| n | benfluthrin |
| o | benfuracarb |
| p | bensultap |
| q | bifenthrin |
| r | bioallethrin |
| s | bioresmethrin |
| t | bistrifluron |
| u | buprofezin |
| v | butocarboxim |
| w | carbaryl |
| x | carbofuran |
| y | carbosulfan |
| z | cartap |
| aa | chlorantraniliprole |
| ab | chlorethoxyfos |
| ac | chlorfenapyr |
| ad | chlorfenvinphos |
| ae | chlorfluazuron |
| af | chlormephos |
| ag | chlorpyrifos |
| ah | chlorpyrifos-methyl |
| ai | chromafenozide |
| aj | clothianidin |
| ak | cyanophos |
| al | cyantraniliprole |
| am | cyclaniliprole |
| an | cycloprothrin |
| ao | cyfluthrin |
| ap | beta-cyfluthrin |
| aq | cyhalothrin |
| ar | gamma-cyhalothrin |
| as | lambda-cyhalothrin |
| at | cypermethrin |
| au | zeta-cypermethrin |
| av | cyphenothrin |
| aw | cyromazine |
| ax | deltamethrin |
| ay | diafenthiuron |
| az | diazinon |
| ba | dichlorvos |
| bb | diflubenzuron |
| bc | dimethoate |
| bd | dimethylvinphos |
| be | dinotefuran |
| bf | diofenolan |
| bg | disulfoton |
| bh | emamectin-benzoate |
| bi | empenthrin |
| bj | endosulfan |
| bk | alpha-endosulfan |
| bl | EPN |
| bm | esfenvalerate |
| bn | ethiofencarb |
| bo | ethiprole |
| bp | etofenprox |
| bq | etrimfos |
| br | fenitrothion |
| bs | fenobucarb |
| bt | fenoxycarb |
| bu | fenthion |
| bv | fenvalerate |
| bw | fipronil |
| bx | flometoquin |
| by | flonicamid |
| bz | fluazuron |

TABLE 1-continued

| No. | Compound Name (Common Name) |
|---|---|
| ca | flubendiamide |
| cb | flucycloxuron |
| cc | flucythrinate |
| cd | flufenerim |
| ce | flufenoxuron |
| cf | flufiprole |
| cg | fluhexafon |
| ch | flumethrin |
| ci | flupyradifurone |
| ck | fluvalinate |
| cl | tau-fluvalinate |
| cm | fonofos |
| cn | furathiocarb |
| co | halofenozide |
| cp | heptafluthrin |
| cq | hexaflumuron |
| cr | hydramethylnon |
| cs | imidacloprid |
| ct | imiprothrin |
| cu | indoxacarb |
| cv | indoxacarb-MP |
| cw | isoprocarb |
| cx | isoxathion |
| cy | lepimectin |
| cz | lufenuron |
| da | malathion |
| db | meperfluthrin |
| dc | metaflumizone |
| dd | metaldehyde |
| de | methacrifos |
| df | methamidophos |
| dg | methidathion |
| dh | methomyl |
| di | methoprene |
| dj | methoxychlor |
| dk | methoxyfenozide |
| dl | metofluthrin |
| dm | muscalure |
| dn | nitenpyram |
| do | novaluron |
| dp | noviflumuron |
| dq | omethoate |
| dr | oxydemeton-methyl |
| ds | parathion-methyl |
| dt | permethrin |
| du | phenothrin |
| dv | phenthoate |
| dw | phorate |
| dx | phosalone |
| dy | phosmet |
| dz | phoxim |
| ea | pirimicarb |
| eb | pirimiphos-methyl |
| ec | profenofos |
| ed | prothiofos |
| ee | pymetrozine |
| ef | pyrifluquinazon |
| eg | pyriprole |
| eh | pyriproxyfen |
| ei | resmethrin |
| ej | rotenone |
| ek | silafluofen |
| el | spinetoram |
| em | spinosad |
| en | spirotetramat |
| eo | sulfotep |
| ep | sulfoxaflor |
| eq | tebufenozide |
| er | teflubenzuron |
| es | tefluthrin |
| et | terbufos |
| eu | tetrachlorvinphos |
| ev | tetramethrin |
| ew | d-tetramethrin |
| ex | tetramethylfluthrin |
| ey | tetraniliprole |
| ez | thiacloprid |
| fa | thiamethoxam |
| fb | thiocyclam |
| fc | thiodicarb |
| fd | thiofanox |
| fe | thiometon |
| ff | tolfenpyrad |
| fg | triflumuron |
| fh | NC-515 |
| fi | ME5382 |
| fj | MIE-1209 |
| fk | ZDI-2501 |
| fl | acequinocyl |
| fm | acrinathrin |
| fn | amidoflumet |
| fo | amitraz |
| fp | azocyclotin |
| fq | benzoximate |
| fr | bifenazate |
| fs | bromopropylate |
| ft | clofentezine |
| fu | cyenopyrafen |
| fv | cyflumetofen |
| fw | dicofol |
| fx | dienochlor |
| fy | etoxazole |
| fz | fenazaquin |
| ga | fenbutatin oxide |
| gb | fenpyroximate |
| gc | fluacrypyrim |
| gd | formetanate |
| ge | halfenprox |
| gf | hexythiazox |
| gg | milbemectin |
| gh | propargite |
| gi | spirodiclofen |
| gj | spiromesifen |
| gk | tebufenpyrad |
| gl | NA-89 |
| gm | benalaxyl |
| gn | benalaxyl-M |
| go | furalaxyl |
| gp | metalaxyl |
| gq | metalaxyl-M |
| gr | ofurace |
| gs | oxadixyl |
| gt | bupirimate |
| gu | ethirimol |
| gv | hymexazol |
| gw | benomyl |
| gx | carbendazim |
| gy | fuberidazole |
| gz | thiabendazole |
| ha | thiophanate-methyl |
| hb | diethofencarb |
| hc | ethaboxam |
| hd | zoxamide |
| he | pencycuron |
| hf | fluopicolide |
| hg | diflumetorim |
| hi | benodanil |
| hj | benzovindiflupyr |
| hk | bixafen |
| hl | boscalid |
| hm | carboxin |
| hn | fenfuram |
| ho | fluopyram |
| hp | flutolanil |
| hq | fluxapyroxad |
| hr | furametpyr |
| hs | isofetamide |
| ht | isopyrazam |
| hu | mepronil |
| hv | oxycarboxin |
| hw | penflufen |
| hx | penthiopyrad |
| hy | sedaxane |
| hz | thifluzamide |
| ia | azoxystrobin |
| ib | coumoxystrobin |

TABLE 1-continued

| No. | Compound Name (Common Name) |
|---|---|
| ic | dimoxystrobin |
| ie | enestrobin |
| if | enoxastrobin |
| ig | famoxadone |
| ih | fenamidone |
| ii | fenaminstrobin |
| ij | flufenoxystrobin |
| ik | fluoxastrobin |
| il | kresoxim-methyl |
| im | mandestrobin |
| in | metominostrobin |
| io | orysastrobin |
| ip | pyrametostrobin |
| iq | pyraoxystrobin |
| ir | pyribencarb-methyl |
| is | pyriminostrobin |
| it | triclopyricarb |
| iu | trifloxystrobin |
| iv | amisulbrom |
| iw | cyazofamid |
| ix | dinocap |
| iy | fluazinam |
| iz | meptyldinocap |
| ja | fentin |
| jb | tributyltin oxide |
| jc | silthiofam |
| jd | ametoctradin |
| je | cyprodinil |
| jf | mepanipyrim |
| jg | pyrimethanil |
| jh | blasticidin-s |
| ji | kasugamycin |
| jk | proquinazid |
| jl | quinoxyfen |
| jm | fenpiclonil |
| jn | fludioxonil |
| jo | chlozolinate |
| jp | iprodione |
| jq | procymidone |
| jr | vinclozolin |
| js | edifenphos |
| jt | iprobenfos |
| ju | isoprothiolane |
| jv | pyrazophos |
| jw | biphenyl |
| jx | chloroneb |
| jy | dicloran |
| jz | etridiazole |
| ka | quintozene |
| kb | tecnazene |
| kc | tolclofos-methyl |
| kd | Bacillus subtilis |
| ke | azaconazole |
| kf | bitertanol |
| kg | bromuconazole |
| kh | climbazole |
| ki | diclobutrazol |
| kj | difenoconazole |
| kl | diniconazole |
| km | diniconazole-M |
| kn | epoxiconazole |
| ko | etaconazole |
| kp | fenarimol |
| kq | fenbuconazole |
| kr | fluotrimazole |
| ks | fluquinconazole |
| kt | flusilazole |
| ku | flutriafol |
| kv | furconazole |
| kw | hexaconazole |
| kx | imazalil |
| ky | imibenconazole |
| kz | ipconazole |
| la | metconazole |
| lb | myclobutanil |
| lc | nuarimol |
| ld | oxpoconazole fumarate |
| le | pefurazoate |

TABLE 1-continued

| No. | Compound Name (Common Name) |
|---|---|
| lf | penconazole |
| lg | prochloraz |
| lh | propiconazole |
| li | prothioconazole |
| lj | pyrifenox |
| lk | pyrisoxazole |
| ll | simeconazole |
| lo | tebuconazole |
| lp | tetraconazole |
| lq | triadimefon |
| lr | triadimenol |
| ls | triflumizole |
| lt | triforine |
| lu | triticonazole |
| lv | aldimorph |
| lw | dodemorph-acetate |
| lx | fenpropidin |
| ly | fenpropimorph |
| lz | piperalin |
| ma | spiroxamine |
| mb | tridemorph |
| mc | fenhexamid |
| md | fenpyrazamine |
| me | validamycin |
| mf | polyoxins |
| mg | polyoxin-D |
| mh | benthiavalicarb-isopropyl |
| mi | dimethomorph |
| mj | flumorph |
| mk | iprovalicarb |
| ml | mandipropamid |
| mm | pyrimorph |
| mn | valifenalate |
| mo | phthalide |
| mp | pyroquilon |
| mq | tricyclazole |
| mr | carpropamid |
| ms | diclocymet |
| mt | fenoxanil |
| mu | acibenzolar-S-methyl |
| my | probenazole |
| mw | isotianil |
| mx | tiadinil |
| my | laminarin |
| mz | bordeaux mixture |
| na | cheshunt mixture |
| nb | basic copper carbonate |
| nc | copper hydroxide |
| nd | copper naphthenate |
| ne | copper oleate |
| nf | copper oxychloride |
| ng | copper sulfate |
| nh | basic copper sulfate |
| ni | oxine copper |
| nj | calcium polysulfide |
| nk | sulfur |
| nl | amobam |
| nm | ferbam |
| nn | mancozeb |
| no | maneb |
| np | metiram |
| nq | polycarbamate |
| nr | propineb |
| ns | thiram |
| nt | ziram |
| nu | captan |
| nv | folpet |
| nw | chlorothalonil |
| nx | dichlofluanid |
| ny | tolylfluanid |
| nz | guazatine |
| oa | iminoctadine-albesilate |
| ob | iminoctadine-triacetate |
| oc | anilazine |
| od | dithianon |
| oe | chinomethionat |
| of | fluoroimide |
| og | cyflufenamid |

TABLE 1-continued

| No. | Compound Name (Common Name) |
| --- | --- |
| oh | cymoxanil |
| oi | diclomezine |
| oj | dodine |
| ok | ferimzone |
| ol | flusulfamide |
| om | flutianil |
| on | fosetyl-aluminium |
| oo | metrafenone |
| op | oxathiapiprolin |
| oq | picarbutrazox |
| or | pyriofenone |
| os | tebufloquin |
| ot | tolprocarb |
| ou | triazoxide |
| ov | potassium hydrogen carbonate |
| ow | sodium hydrogen carbonate |
| ox | Chinese mushroom mycelium extract |
| oy | Chinese mushroom carpophore extract |
| oz | BCF-082 |
| pa | NNF-0721 |
| pb | ZF-9646 |

The characteristics of the composition of the present invention and the method of the present invention are as follows. First, insecticidal, miticidal, nematicidal, molluscicidal, microbicidal, or bactericidal effects are clearly enhanced compared to when those chemicals are used individually, and rapid insecticidal, miticidal, nematicidal, molluscicidal, microbicidal, or bactericidal effects are given. Second, broad insecticidal, miticidal, nematicidal, molluscicidal, microbicidal, or bactericidal spectra and longer residual activities are induced, which have not been seen in any of the conventional insecticides, miticides, nematicides, molluscicides, microbicides, and bactericides. Third, spraying amounts can be reduced compared to when those chemicals are used individually.

That is, the composition of the present invention and the method of the present invention provide synergistic insecticidal, miticidal, nematicidal, molluscicidal, microbicidal, or bactericidal effects. The synergistic insecticidal, miticidal, nematicidal, molluscicidal, microbicidal, or bactericidal effects cannot be expected from an individual insecticidal, miticidal, nematicidal, molluscicidal, microbicidal, or bactericidal effect that each of the chemicals provides, and thus usefulness of the composition of the present invention and the method of the present invention is that the certain control effects can be provided to a variety of pests than the case where each of the compounds is used individually.

Among the compounds shown in Table 1 above, the compounds whose control effects are synergistically improved in combination with the first active ingredient compound I are shown in Table 2.

TABLE 2

| No. | Compound Name (Common Name) | No. | Compound Name (Common Name) |
| --- | --- | --- | --- |
| aa | chlorantraniliprole | al | cyantraniliprole |
| am | cyclaniliprole | ar | gamma-cyhalothrin |
| ca | flubendiamide | ey | tetraniliprole |
| em | spinosad | el | spinetoram |
| dc | metaflumizone | ci | flupyradifurone |
| bx | flometoquin | q | bifenthrin |
| ce | flufenoxuron | | |

The one or two first active ingredient compound(s) I and the one or more second active ingredient compound(s) II in the present invention can be applied to a variety of methods as described below.

1. Simultaneous applications, that is,
  a) Mixed applications (i.e., for example, as mixtures for immediate uses such as formula, or mixtures in tanks) and
  b) Individual applications (i.e., applications with individual tanks), or,
2. Sequential individual applications, in which order of the applications generally does not affect the results of the control method in any way.

Accordingly, the method for controlling harmful organism, mites, nematodes, molluscs, harmful microbes, and bacteria is conducted by applying at least one of the first active ingredient compounds I and at least one of the second active ingredient compounds II separately or together, or applying a mixture of at least one of the first active ingredient compounds I and at least one of the second active ingredient compounds II to seeds, plants, or soil by spraying or dusting, before or after seeding, or before or after budding of the plants.

In the composition of the present invention and the method of the present invention, the optimal mixing ratio (ratio by weight) of the first active ingredient compound I and the second active ingredient compound II is within a range of 100:1 to 1:100, preferably 20:1 to 1:20, and particularly 10:1 to 1:10, depending on characteristics of the compounds.

In the composition of the present invention and the method of the present invention, although the preferable treating amounts of the active ingredient compounds vary depending on types of the pests to be controlled, it is usually 0.1 g ai/ha to 1,000 g ai/ha for the first active ingredient compound I and 0.1 g ai/ha to 1,000 g ai/ha for the second active ingredient compound II; and preferably 1 g ai/ha to 300 g ai/ha for the former and 1 g ai/ha to 300 g ai/ha for the latter.

The composition of the present invention can be applied to "agricultural pests" and "agricultural diseases" which inflict horticultural crops, trees, and the like; "livestock pests" that are parasitic to livestock and poultry; "sanitary pests" that adversely affect living environments of humans, such as houses; and mites, nematodes, and molluscs, which rise and inflict in such situations. Specific examples of the pests, mites, nematodes, molluscs, and diseases which can be controlled with the composition of the present invention will be listed below, but not limited thereto.

Examples of the pests are as follows. Hymenoptera insects, such as Chestnut gall wasp (*Dryocosmus kuriphilus*), Argentine ant (*Linepithema humile*), Army ant (*Eciton burchelli, E. schmitti*), Japanese carpenter ant (*Camponotus japonicus*), Pharaoh ant (*Monomorium pharaonis*), Bulldog ant (*Myrmecia* spp.), Fire ant (*Solenopsis* spp.), Asian giant hornet (*Vespa mandarina*), Japanese yellow hornet (*Vespa simillima*), Large rose sawfly (*Arge pagana*), European pine sawfly (*Neodiprion sertifer*), Chestnut sawfly (*Apethymus kuri*), Cabbage sawfly (*Athalia infumata*), and Turnip sawfly (*Athalia rosae*).

Lepidoptera insects, such as Pear leaf miner (*Bucculatrix pyrivorella*), Tea leafroller (*Caloptilia theivora*), Apple leafminer (*Phyllonorycter ringoniella*), Citrus leafminer (*Phyllocnistis citrella*), Sweetpotato leaffolder (*Helcystogramma triannulella*), Pink bollworm (*Pectinophora gossypiella*), Persimmon fruit moth (*Stathmopoda masinissa*), Peach fruit moth (*Carposina sasakii*), Allium leafminer (*Acrolepiopsis sapporensis*), Yam leafminer (*Acrolepiopsis suzukiella*), Peach leafminer (*Lyonetia clerkella*), *Lyonetia prunifoliella malinella*, Diamondback moth (*Plutella xylostella*), Rice stem borer (*Chilo suppressalis*), Bluegrass webworm (*Para-*

*pediasia teterrella*), Cabbage webworm (*Hellula undalis*), Rice leafroller (*Cnaphalocrocis medinalis*), Yellow peach moth (*Conogethes punctiferalis*), Cucumber moth (*Diaphania indica*), Mulberry pyralid (*Glyphodes pyloalis*), Asian corn borer (*Ostrinia furnacalis*), European corn borer (*Ostrinia nubilalis*), Adzuki bean borer (*Ostrinia scapulalis*), Lesser corn stalk borer (*Elasmopalpus lignosellus*), Limabean pod borer (*Etiella zinckenella*), Peach tree borer (*Synanthedon exitiosa*), Cherry tree borer (*Synanthedon hector*), *Toleria romanovi*, Oriental moth (*Monemaflavescens*), *Parasa consocia, Parasa lepida, Parasa siniea, Artona martini, Illiberis pruni, Illiberis rotundata*, Carpenter moth (*Cossus insularis*), Codling moth (*Cydiapomonella*), Plum fruit moth (*Grapholita dimorpha*), Oriental fruit moth (*Grapholita molesta*), Soybean pod borer (*Leguminivora glycinivorella*), Soybean podworm (*Matsumuraeses phaseoli*), Grape berry moth (*Endopiza viteana*), Smaller tea *tortrix* (*Adoxophyes honmai*), Summer fruit *tortrix* (*Adoxophyes oranafasciata*), Asiatic leafroller (*Archips breviplicanus*), Apple *tortrix* (*Archipsfuscocupreanus*), Oriental tea *tortrix* (*Homona magnanima*), Dark fruit-tree *tortrix* (*Pandemis heparana*), Pine moth (*Dendrolimus spectabilis*), Japanese hemlock caterpillar (*Dendrolimus superans*), Japanese bamboo lappet moth (*Euthrix albomaculata*), Drinker moth (*Euthrixpotatoria*), Oriental lappet (*Gastropacha orientalis*), Kunugia undans, Kunugia yamadai, Tomato hornworm (*Manduca quinquemaculata*), Tobacco hornworm (*Manduca sexta*), Fall webworm moth (*Hyphantria cunea*), Mulberry tiger moth (*Lemyra imparilis*), *Eilema fuscodorsalis, Eilema laevis*, Oriental tussock moth (*Artaxa subflava*), Euproctis *piperita*, Tea tussock moth (*Euproctis pseudoconspersa*), Swan moth (*Sphrageidus similis*), Gypsy moth (*Lymantria dispar*), White-spotted tussock moth (*Orgyia thyellina*), Rice green caterpillar (*Naranga aenescens*), *Adris tyrannus*, Sweet potato leaf worm (*Aedia leucomelas*), Cabbage armyworm (*Mamestra brassicae*), Oriental armyworm (*Pseudaletia separata*), Lawn grass cutworm (*Spodoptera depravata*), Southern armyworm (*Spodoptera eridania*), Beet armyworm (*Spodoptera exigua*), Fall armyworm (*Spodoptera fugiperda*), Cotton leafworm (*Spodoptera littoralis*), Common cutworm (*Spodoptera litura*), Cotton bollworm (*Helicoverpa armigera*), Oriental tobacco budworm (*Helicoverpa assulta*), Tobacco budworm (*Heliothis virescens*), Corn earworm (*Helicoverpa zea*), Black cutworm (*Agrotis ipsilon*), Turnip moth (*Agrotis segetum*), Asiatic common looper (*Autographa nigrisigna*), Threespotted plusia (*Ctenoplusia agnata*), Soybean looper (*Pseudoplusia includens*), Cabbage looper (*Trichoplusia ni*), Japanese giant looper (*Ascotis selenaria*), Large white (*Pieris brassicae*), Cabbage white butterfly (*Pieris rapae crucivora*), Straight swift (*Parnara guttata*), cotton leafworm (*Alabama argillacea*), and sugarcane borer (*Diatraea sacharalis*).

Diptera insects, such as Melon fly (*Bactrocera cucurbitae*), Oriental fruit fly (*Bactrocera dorsalis*), Queensland fruit fly (*Bactrocera tryoni*), Japanese orange fly (*Bactrocera tsuneonis*), Mediterranean fruit fly (*Ceratitis capitata*), Mexican fruit fly (*Anastrepha ludens*), Apple maggot (*Rhagoletispomonella*), Rice leaf miner (*Agromyza oryzae*), Pea leaf miner (*Chromatomyia horticola*), Cabbage leafminer (*Liriomyza brassicae*), Tomato leaf miner (*Liriomyza bryoniae*), Stone leek leafminer (*Liriomyza chinensis*), Pea leafminer (*Liriomyza huidobrensis*), Tomato leafminer (*Liriomyza sativae*), Serpentine leafminer (*Liriomyza trifolii*), Japanese fruit fly (*Drosophila suzukii*), Smaller rice leaf miner (*Hydrellia griseola*), Tsetse fly (*Glossina morsitans, G palpalis*), Forest fly (*Hippobosca equina*), Sheep ked (*Melophagus ovinus*), Onion fly (*Delia antiqua*), Seed corn maggot (*Delia platura*), Beet leaf miner (*Pegomya cunicularia*), Lesser house fly (*Fannia canicularis*), Sheep headfly (*Hydrotaea irritans*), Sweat fly (*Morellia simplex*), Face fly (*Musca autumnalis*), Housefly (*Musca domestica*), Australian bush fly (*Musca vetustissima*), Horn fly (*Haematobia irritans*), Stable fly (*Stomoxys calcitrans*), *Calliphora lata*, Bottle fly (*Calliphora vicina*), Old World screw-worm fly (*Chrysomya bezziana*), Blow fly (*Chrysomya chloropyga*), Oriental latrine fly (*Chrysomya megacephala*), New World screw-worm fly (*Cochliomyia hominivorax*), Black blow fly (*Phormia regina*), Northern blowfly (*Protophormia terraenovae*), Australian sheep blowfly (*Lucilia cuprina*), Green bottle fly (*Lucilia illustris*), Common green bottle fly (*Lucilia sericata*), Bot flies (*Cuterebra* spp.), Human botfly (*Dermatobia hominis*), Horse nose bot fly (*Gasterophilus haemorrhoidalis*), Horse bot fly (*Gasterophilus intestinalis*), Throat bot fly (*Gasterophilus nasalis*), Warble fly (*Hypoderma bovis*), Common cattle grub (*Hypoderma lineatum*), Sheep nasal bot fly (*Oestrus ovis*), Flesh fly (*Sarcophaga carnaria*), Flesh fly (*Sarcophaga peregrina*), Splayed deerfly (*Chrysops caecutiens*), Deer fly (*Chrysops suavis*), Common horse fly (*Haematopota pluvialis*), Greenhead horse fly (*Tabanus nigrovittatus*), Horse fly (*Tabanus trigonus*), Soybean pod gall midge (*Asphondylia yushimai*), Hessian fly (*Mayetiola destructor*), Orange wheat blossom midge (*Sitodiplosis mosellana*), Biting midge (*Culicoides arakawae*), Black gnat (*Leptoconops nipponensis*), *Prosimulium yezoensis*, Black fly (*Simulium ochraceum*), African malaria mosquito (*Anopheles gambiae*), *Anopheles* hyrcanus sinesis, *Anopheles lesteri*, Yellow fever mosquito (*Aedes aegypti*), Asian tiger mosquito (*Aedes albopictus*), House mosquito (*Culex pipiens molestus*), House mosquito (*Culex pipiens pallens*), *Culex tritaeniorhynchus*, Sandfly (*Phlebotomus* spp.), and Moth fly (*Telmatoscopus albipunctatus*).

Siphonaptera insects, such as Hen flea (*Ceratophyllus gallinae*), Chigoe flea (*Tungapenetrans*), Dog flea (*Ctenocephalides canis*), Cat flea (*Ctenocephalides felis*), Sticktight flea (*Echidnophaga gallinacea*), Human flea (*Pulex irritans*), and Oriental rat flea (*Xenopsylla cheopis*).

Coleoptera insects, such as Tobacco beetle (*Lasioderma serricorne*), Common bean weevil (*Acanthoscelides obtectus*), Adzuki bean beetle (*Callosobruchus chinensis*), Grape borer (*Xylotrechuspyrrhoderus*), Asian long-horn beetle (*Anoplophora glabripennis*), White-spotted longicorn beetle (*Anoplophora malasiaca*), Japanese pine sawyer (*Monochamus alternatus*), Yellow-spotted longicorn beetle (*Psacothea hilaris*), Colorado potato beetle (*Leptinotarsa decemlineata*), Mustard leaf beetle (*Phaedon cochleariae*), Rice leaf beetle (*Oulema oryzae*), Reaf beetle (*Demotinafasciculata*), Cucurbit leaf beetle (*Aulacophora femoralis*), Beet flea beetle (*Chaetocnema concinna*), Northern corn rootworm (*Diabrotica barberi*), Southern corn rootworm (*Diabrotica undecimpunctata*), Western corn rootworm (*Diabrotica virgifera*), Striped flea beetle (*Phyllotreta striolata*), *Solanum* flea beetle (*Psylliodes angusticollis*), Mexican been beetle (*Epilachna varivestis*), Large twenty-eight-spotted ladybird (*Epilachna vigintioctomaculata*), Twentyeight-spotted ladybird (*Epilachna vigintioctopunctata*), Epuraea domina, Pollen beetle (*Meligethes aeneus*), Peach curculio (*Rhynchites heros*), Sweetpotato weevil (*Cylas formicarius*), West Indian sweet potato weevil (*Euscepes postfasciatus*), Boll weevil (*Anthonomus grandis*), White-fringed beetle (*Graphognatus leucoloma*), Black vine weevil (*Otiorhynchus sulcatus*), Alfalfa weevil (*Hyperapostica*), Granary weevil (*Sitophilus granarius*), Maize weevil (*Sitophilus zeamais*), Hunting billbug (*Sphenophorus venatus vestitus*), Rice plant weevil (*Echinocnemus squameus*), Rice water weevil (*Lissohoptrus oryzophilus*), Yellow mealworm (*Tenebrio molitor*), Red flour beetle (*Tribolium castaneum*), Sweetpotato wireworm (*Melanotus fortnumi*), Sugarcane wireworm (*Melanotus tamsuyensis*), Citrus flower chafer (*Gamnetisjucunda*), Yellowish elongate chafer (*Heptophyllapicea*), Cupreous chafer (*Anomala cuprea*), Soybean beetle (*Anomala rufocuprea*), Japanese beetle (*Popillia japonica*), and Rove beetle (*Paederusfuscipes*).

Hemiptera insects, such as Asian *citrus* psyllid (*Diaphorina citri*), Pear sucker (*Psylla pyrisuga*), Camellia spiny whitefly (*Aleurocanthus camelliae*), Orange spiny whitefly (*Aleurocanthus spiniferus*), Silverleaf whitefly (*Bemisia argentifolii*), Sweetpotato whitefly (*Bemisia tabaci*), Citrus whitefly (*Dialeurodes citri*), Greenhouse whitefly (*Trialeurodes vaporariorum*), Pea aphid (*Acyrthosiphon pisum*), Cowpea aphid (*Aphis craccivora*), Black bean aphid (*Aphis fabae*), Soybean aphid (*Aphis glycines*), Cotton aphid (*Aphis gossypii*), Green apple aphid (*Aphispomi*), *Spiraea* aphid (*Aphis spiraecola*), Foxglove aphid (*Aulacorthum solani*), Leafcurl plum aphid (*Brachycaudus helichrysi*), Cabbage aphid (*Brevicoryne brassicae*), Walnut aphid (*Chromaphis juglandicola*), Russian wheat aphid (*Diuraphis noxia*), Rosy apple aphid (*Dysaphis plantaginea*), Mealy plum aphid (*Hyalopteruspruni*), Turnip aphid (*Lipaphis erysimi*), Potato aphid (*Macrosiphum euphorbiae*), Blackmargined aphid (*Monellia caryella*), Green peach aphid (*Myzus persicae*), Lettuce aphid (*Nasonovia ribisnigri*), Onion aphid (*Neotoxoptera formosana*), Bird cherry-oat aphid (*Rhopalosiphum padi*), Rice root aphid (*Rhopalosiphum rufiabdominalis*), Corn leaf aphid (*Sitobion akebiae*), English grain aphid (*Sitobion avenae*), Greenbug (*Schizaphis graminum*), Black *citrus* aphid (*Toxoptera aurantii*), Brown *citrus* aphid (*Toxoptera citricida*), Wooly apple aphid (*Eriosoma lanigerum*), Grape *phylloxera* (*Viteus vitifolii*), Indian wax scale (*Ceroplastes ceriferus*), Red wax scale (*Ceroplastes rubens*), Citricola scale (*Coccus pseudomagnoliarum*), California red scale (*Aonidiella aurantii*), San jose scale (*Comstockaspis perniciosa*), Tea scale (*Fiorinia theae*), Peony scale (*Pseudaonidia paeoniae*), Mulberry scale (*Pseudaulacaspis pentagona*), White peach scale (*Pseudaulacaspis prunicola*), Citrus snow scale (*Unaspis citri*), Euonymus scale (*Unaspis euonymi*), Arrowhead scale (*Unaspis yanonensis*), Giant margarodid scale (*Drosicha corpulenta*), Cottony cushion scale (*Iceryapurchasi*), Cotton mealy bug (*Phenacoccus solani*), Citrus mealybug (*Planococcus citri*), Japanese mealybug (*Planococcus kuraunhiae*), Comstock mealybug (*Pseudococcus comstocki*), Grape mealybug (*Pseudococcus maritimus*), Small brown planthopper (*Laodelphax striatella*), Brown rice planthopper (*Nilaparvata lugens*), White-backed rice planthopper (*Sogatella furcifera*), Grape Leafhopper (*Epiacanthus stramineus*), Indian cotton leafhopper (*Amrasca devastans*), Beardsley leafhopper (*Balclutha saltuella*), Aster leafhopper (*Macrosteles fascifrons*), *Macrosteles striifrons*, Green rice leafhopper (*Nephotettix cincticeps*), Grape Leafhopper (*Arboridia apicalis*), Potato Leafhopper (*Empoascafabae*), *Empoasca nipponica*, Tea green leafhopper (*Empoasca onukii*), Bean's smaller green leafhopper (*Empoasca sakaii*), Sloe bug (*Dolycoris baccarum*), Cabbage bug (*Eurydema rugosa*), Whitespotted spined bug (*Eysarcoris aeneus*), *Eysarcoris lewisi*, White-spotted stink bug (*Eysarcoris ventralis*), Sheild bug (*Glaucias subpunctatus*), Brown marmorated stink bug (*Halyomorpha halys*), Eastern green stink bug (*Nezara antennata*), Southern green stink bug (*Nezara viridula*), Redbanded stink bug (*Piezodorus guildinii*), Redbanded shield bug (*Piezodorus hybneri*), Brown-winged green bug (*Plautia crossota*), Japanese black rice bug (*Scotinophora lurida*), Bean bug (*Riptortus clavatus*), Rice bug (*Leptocorisa chinensis*), Rice stink bug (*Cletus punctiger*), Squash bug (*Paradasynus spinosus*), Rhopalid bug (*Rhopalus maculatus*), True chinch bug (*Blissus leucopterus*), Oriental chinch bug (*Cavelerius saccharivorus*), Seed bug (*Togo hemipterus*), Red cotton bug (*Dysdercus cingulatus*), Blood-sucking bug (*Rhodniusprolixus*), Kissing bug (*Triatoma dimidiata*), Kissing bug (*Triatoma infestans*), green stink bug (*Acrosternum hilare*), brown stink bug (*Euschistus servus*), southern green stink bug (*Nezara viridula*), Tarnished plant bug (*Lygus lineolaris*), *Dichelops furcatus*, sugarcane spittlebug (*Mahanarva fimbriolata*), Azalea lace bug (*Stephanitispyrioides*), Bed bug (*Cimex lectularius*), Pale greenplant bug (*Apolygus spinolae*), Western tarnished plant bug (*Lygus hesperus*), Tarnished plant bug (*Lygus lineolaris*), Rice stink bug (*Stenodema sibiricum*), Sorghum plant bug (*Stenotus rubrovittatus*), Rice leaf bug (*Trigonotylus caelestialium*), Island fleahopper (*Halticus insularis*), and Cotton fleahopper (*Pseudatomoscelis seriatus*).

Thysanoptera insects, such as Flower thrips (*Frankliniella intonsa*), Western flower thrips (*Frankliniella occidentalis*), Greenhouse thrips (*Heliothrips haemorrhoidalis*), Yellow tea thrips (*Scirtothrips dorsalis*), Melon thrips (*Thrips palmi*), Onion thrips (*Thrips tabaci*), and Japanese gall-forming thrips (*Ponticulothrips diospyrosi*).

Psocodea insects, such as Body louse (*Menacanthus cornutus*), Small body louse (*Menacanthus pallidulus*), Chicken body louse (*Menacanthus stramineus*), Chicken shaft louse (*Menopon gallinae*), Chicken head louse (*Cuclotogaster heterographa*), Brown chicken louse (*Goniodes dissmilis*), Fluff louse (*Goniodes gallinae*), Large hen louse (*Goniodes gigas*), Wing louse (*Lipeurus caponis*), Cattle chewing louse (*Damalinia bovis*), Cat louse (*Felicola subrostrata*), Dog biting louse (*Trichodectes canis*), Short-nosed cattle louse (*Haematopinus eurysternus*), Tail switch louse (*Haematopinus quadripertusus*), Large pig louse (*Haematopinus suis*), Buffalo louse (*Haematopinus tuberculatus*), Dog sucking louse (*Linognathus setosus*), Long-nosed cattle louse (*Linognathus vituri*), Rabbit louse (*Haemodipsus ventricosus*), Little blue cattle louse (*Solenopotes capillatus*), Head louse (*Pediculus humanus*), Mouse louse (*Polyplax serratus*), and Crab louse (*Pthirus pubis*).

Orthoptera insects, such as Desert locust (*Schistocerca gregaria*), Australian plague locust (*Chortoicetes terminifera*), Migratory locust (*Locusta migratoria*), Lesser paddy grasshopper (*Oxyajaponica*), Rice grasshopper (*Oxya yezoensis*), Emma field cricket (*Teleogryllus emma*), and Oriental mole cricket (*Gryllotalpa orientalis*).

Dictyoptera insects, such as German cockroach (*Blattella germanica*), American cockroach (*Periplaneta americana*), Smoky-brown cockroach (*Periplaneta fuliginosa*), Japanese cockroach (*Periplanetajaponica*), Daikoku dry-wood termite (*Cryptotermes domesticus*), Western dry-wood termite (*Incisitermes minor*), Formosan subterranean termite (*Coptotermesformosanus*), Japanese subterranean termite (*Reticulitermes speratus*), and Black-winged subterranean termite (*Odontotermes formosanus*).

Collembola: Hexapoda, such as Rootfeeding springtail (*Onychiurus folsomi*), *Onychiurus sibiricus*, and Garden springtail (*Bourletiella hortensis*).

Isopoda crustaceans, such as Pill bug (*Armadillidium vulgare*) and Common rough woodlouse (*Porcellio scaber*).

Arguloida crustaceans, such as *Argulus coregoni*, Japanese fishlouse (*Argulusjaponicus*), and *Argulus* scutiformis.

Siphonostomatoida crustaceans, such as Sea louse (*Caligus curtus, C. elongatus*) and Salmon louse (*Lepeophtheirus salmonis*).

Astigmata: Acarina, such as Storage mite (*Glycyphagus destructor*), House itch mite (*Glycyphagus domesticus*), Brown-legged grain mite (*Aleuroglyphus ovatus*), Cheese mite (*Tyrophagus putrescentiae*), Tyrophagus *similis*, Bulb mite (*Rhizoglyphus robini*), Feather mite (*Pterolichus obtusus*), Feather mite (*Megninia cubitalis*), American house dust mite (*Dermatophagoidesfarinae*), House dust mite (*Dermatophagoidespteronyssinus*), Chorioptic mange mite (*Chorioptes bovis*), Dog ear mite (*Otodectes cynotis*), Psoroptic mite (*Psoroptes communis*), Rabbit ear mite (*Psoroptes cuniculi*), Sheep scab mite (*Psoroptes ovis*), Itch mite (*Sarcoptes scabiei*), and Cat mange mite (*Notoedres cati*).

Oribatida: Acarina, such as *Haplochthonius simplex*.

Prostigmata: Acarina, such as *Chelacaropsis moorei, Cheyletiella blakei,* Rabbit fur mite (*Cheyletiella parasitovorax*), *Cheyletiella yasguri, Cheyletus eruditus, Cheyletus malaccensis*, Dog follicle mite (*Demodex canis*), Cat follicle mite (*Demodex cati*), Face mite (*Demodexfolliculorum*), Wheat curl mite (*Aceria tulipae*), Pear rust mite (*Eriophyes chibaensis*), Peach bud mite (*Eriophyes insidiosus*), Pearleaf blister mite (*Eriophyespyri*), Tea rust mite (*Acaphylla theavagrans*), Tomato russet mite (*Aculops lycopersici*), Pink citrus rust mite (*Aculopspelekassi*), Apple rust mite (*Aculus schlechtendali*), Citrus rust mite (*Phyllocoptruta oleivora*), Broad mite (*Polyphagotarsonemus latus*), Cyclamen mite (*Phytonemuspallidus*), Tarsonemid mite (*Tarsonemus bilobatus*), *Oligonychus shinkajii,* Citrus red mite (*Panonychus citri*), Spider mite (*Panonychus mori*), European red mite (*Panonychus ulmi*), Kanzawa spider mite (*Tetranychus kanzawai*), Two-spotted spider mite (*Tetranychus urticae*), *Penthaleus erythrocephalus*, Winter grain mite (*Penthaleus major*), *Eutrombicula wichmanni,* Trombiculid mite (*Helenicula miyagawai*), *Leptotrombidium akamushi, Leptotrombidium pallida*, and Tsutsugamushi mite (*Leptotrombidium scutellare*).

Metastigmata: Acarina, such as English fowl tick (*Argas persicus*), Soft tick (*Ornithodoros moubata*), Relapsing fever tick (*Ornithodoros turicata*), Spinose ear tick (*Otobius megnini*), Lone star tick (*Amblyomma americanum*), Gulf coast tick (*Amblyomma maculatum*), *Haemaphysalis campanulata, Haemaphysalis flava*, Bush tick (*Haemaphysalis longicornis*), *Haemaphysalis* megaspinosa, Tortoise tick (*Hyalomma aegyptium*), Mediterranean tick (*Hyalomma marginatum*), Tropical cattle tick (*Boophilus microplus*), *Ixodes nipponensis, Ixodes ovatus,* Western black-legged tick (*Ixodes pacifcus*), Taiga tick (*Ixodes persulcatus*), Castor bean tick (*Ixodes ricinus*), Black-legged tick (*Ixodes scapularis*), Tropical horse tick (*Anocentor nitens*), Rocky Mountain wood tick (*Dermacentor andersoni*), Pacific Coast tick (*Dermacentor occidentalis*), Ornate cow tick (*Dermacentor reticulatus*), American dog tick (*Dermacentor variabilis*), Rhipicentor spp., American cattle tick (*Rhipicephalus annulatus*), and Brown dog tick (*Rhipicephalus sanguineus*).

Mesostigmata: Acarina, such as Red mite (*Dermanyssus gallinae*), Tropical rat mite (*Ornithonyssus bacoti*), Northern fowl mite (*Ornithonyssus sylviarum*), Honeybee mite (*Varroa destructor*), and Varroa mite (*Varroajacobsoni*).

Architaenioglossa: Gastropoda, such as Apple snail (*Pomacea canaliculata*).

Stylommatophora: Gastropoda, such as Giant African snail (*Achatina fitica*), Terrestrial slug (*Limax marginatus*), Slug (*Meghimatium bilineatum*), Korean round snail (*Acusta despecta sieboldiana*), and Land snail (*Euhadra peliomphala*).

Enoplida Nematoda, such as Giant kidney worm (*Dioctophyma renale*), Thread worms (*Capillaria annulata*), Cropworm (*Capillaria contorta*), Capillary liver worm (*Capillaria hepatica*), *Capillaria perforans, Capillaria philippinensis, Capillaria* suis, Whipworm (*Trichuris discolor*), Whipworm (*Trichuris ovis*), Pig whipworm (*Trichuris suis*), Human whipworm (*Trichuris trichiura*), Dog whipworm (*Trichuris vulpis*), and Pork worm (*Trichinella spiralis*).

Rhabditida Nematoda, such as Intestinal threadworm (*Strongyloides papillosus*), *Strongyloides* planiceps, Pig threadworm (*Strongyloides ransomi*), Threadworm (*Strongyloides stercoralis*), and Micronema spp.

Strongylida Nematoda, such as Hookworm (*Ancylostoma braziliense*), Dog hookworm (*Ancylostoma caninum*), Old World hookworm (*Ancylostoma duodenale*), Cat hookworm (*Ancylostoma tubaeforme*), The Northern hookworm of dogs (*Uncinaria stenocephala*), Cattle hookworm (*Bunostomum phlebotomum*), Small ruminant hookworm (*Bunostomum trigonocephalum*), New World hookworm (*Necator americanus*), *Cyathostomum* spp., *Cylicocyclus* spp., *Cylicodontophorus* spp., *Cylicostephanus* spp., *Strongylus asini, Strongylus edentatus,* Blood worm (*Strongylus equinus*), Blood worm (*Strongylus vulgaris*), Large-mouthed bowel worm (*Chabertia ovina*), Nodular worm (*Oesophagostomum brevicaudatum*), Nodule worm (*Oesophagostomum columbianum*), Nodule worm (*Oesophagostomum dentatum*), Nodular worm (*Oesophagostomum georgianum*), Nodular worm (*Oesophagostomum maplestonei*), Nodular worm (*Oesophagostomum quadrispinulatum*), Nodular worm (*Oesophagostomum radiatum*), Nodular worm (*Oesophagostomum venulosum*), *Syngamus skrjabinomorpha,* Gapeworm (*Syngamus trachea*), Swine kidney worm (*Stephanurus dentatus*), Cattle bankrupt worm (*Cooperia oncophora*), Red stomach worm (*Hyostrongylus rubidus*), Stomach hair worm (*Trichostrongylus axei*), *Trichostrongylus colubriformis,* Oriental trichostrongylus (*Trichostrongylus orientalis*), Red stomach worm (*Haemonchus contortus*), Cattle stomach worm (*Mecistocirrus digitatus*), Brown stomach worm (*Ostertagia ostertagi*), Common lungworm (*Dictyocaulus filaria*), Bovine lungworm (*Dictyocaulus viviparus*), Thin-necked intestinal worm (*Nematodirus filicollis*), Swine lungworm (*Metastrongylus elongatus*), Lungworm (*Filaroides hirthi*), Lungworm (*Crenosoma aerophila*), Fox lungworm (*Crenosoma vulpis*), Rat lung worm (*Angiostrongylus cantonensis*), French heartworm (*Angiostrongylus vasorum*), and *Protostrongylus* spp.

Aphelenchida Nematoda, such as Rice white tip nematode (*Aphelenchoides besseyi*) and Pine wood nematode (*Bursaphelenchus xylophilus*).

Tylenchida Nematoda, such as Potato cyst nematode (*Globodera rostochiensis*), Cereal cyst nematode (*Heterodera avenae*), Soybean cyst nematode (*Heterodera glycines*), Peanut root-knot nematode (*Meloidogyne arenaria*), Northern root-knot nematode (*Meloidogyne hapla*), Southern root-knot nematode (*Meloidogyne incognita*), Javanese root-knot nematode (*Meloidogyne javanica*), Coffee root-lesion nematode (*Pratylenchus coffeae*), Tea root-lesion nematode (*Pratylenchus loosi*), Cobb's root-lesion nematode (*Pratylenchuspenetrans*), and Walnut root-lesion nematode (*Pratylenchus vulnus*).

Oxyurida Nematoda, such as Pinworm (*Enterobius vermicularis*), Equine pinworm (*Oxyuris equi*), and Rabbit pinworm (*Passalurus ambiguus*).

Ascaridida Nematoda, such as Pig roundworm (*Ascaris suum*), Horse roundworm (*Parascaris equorum*), Dog roundworm (*Toxascaris leonina*), Dog intestinal roundworm (*Toxocara canis*), Feline roundworm (*Toxocara cati*), Large cattle roundworm (*Toxocara vitulorum*), *Anisakis* spp., *Pseudoterranova* spp., Caecal worm (*Heterakis gallinarum*), and Chicken roundworm (*Ascaridia galli*).

Spirurida Nematoda, such as Guinea worm (*Dracunculus medinensis*), *Gnathostoma doloresi*, *Gnathostoma hispidum*, *Gnathostoma nipponicum*, Reddish-coloured worm (*Gnathostoma spinigerum*), Dog stomach worm (*Physaloptera canis*), Cat stomach worm (*Physaloptera felidis*, *P. praeputialis*), Feline/canine stomach worm (*Physaloptera rara*), Eye worm (*Thelazia callipaeda*), Bovine eyeworm (*Thelazia rhodesi*), Large mouth stomach worm (*Draschia megastoma*), Equine stomach worm (*Habronema microstoma*), Stomach worm (*Habronema muscae*), Gullet worm (*Gongylonema pulchrum*), Thick stomach worm (*Ascarops strongylina*), Parafilaria (*Parafilaria bovicola*), *Parafilaria multipapillosa*, *Stephanofilaria okinawaensis*, Bancroft filaria (*Wuchereria bancrofti*), *Brugia malayi*, Neck threadworm (*Onchocerca cervicalis*), *Onchocerca gibsoni*, Cattle filarial worm (*Onchocerca gutturosa*), *Onchocerca volvulus*, Bovine filarial worm (*Setaria digitata*), Peritoneal worm (*Setaria equina*), *Setaria labiatopapillosa*, *Setaria marshalli*, Dog heartworm (*Dirofilaria immitis*), and African eye worm (*Loa loa*).

Acanthocephala, such as *Moniliformis moniliformis* and Giant thorny-headed worm (*Macracanthorhynchus hirudinaceus*).

Pseudophyllidean cestodes, such as Fish tapeworm (*Diphyllobothrium latum*), *Diphyllobothrium nihonkaiense*, Manson tapeworm (*Spirometra erinaceieuropaei*), and *Diplogonoporus grandis*.

Cyclophyllidean cestodes, such as *Mesocestoides lineatus*, Chicken tapeworm (*Raillietina cesticillus*), Fowl tapeworm (*Raillietina echinobothrida*), Chicken tapeworm (*Raillietina tetragona*), Canine tapeworm (*Taenia hydatigena*), Canine tapeworm (*Taenia multiceps*), Sheep measles (*Taenia ovis*), Dog tapeworm (*Taenia pisiformis*), Beef tapeworm (*Taenia saginata*), Tapeworm (*Taenia serialis*), Pork tapeworm (*Taenia solium*), Feline tapeworm (*Taenia taeniaeformis*), Hydatid tapeworm (*Echinococcus granulosus*), Small fox tapeworm (*Echinococcus multilocularis*), *Echinococcus oligarthrus*, *Echinococcus vogeli*, Rat tapeworm (*Hymenolepis diminuta*), Dwarf tapeworm (*Hymenolepis nana*), Double-pored dog tapeworm (*Dipylidium caninum*), *Amoebotaenia sphenoides*, *Choanotaenia infundibulum*, *Metroliasthes coturnix*, Equine tapeworm (*Anoplocephala magna*), Cecal tapeworm (*Anoplocephala perfoliata*), Dwarf equine tapeworm (*Paranoplocephala mamillana*), Common tapeworm (*Moniezia benedeni*), Sheep tapeworm (*Moniezia expansa*), and *Stilesia* spp.

Strigeidida trematodes, such as Pharyngostomum cordatum, Blood fluke (*Schistosoma haematobium*), Blood fluke (*Schistosomajaponicum*), and Blood fluke (*Schistosoma mansoni*).

Echinostomida trematodes, such as *Echinostoma cinetorchis*, *Echinostoma hortense*, Giant liver fluke (*Fasciola gigantica*), Common liver fluke (*Fasciola hepatica*), *Fasciolopsis buski*, and *Homalogaster paloniae*.

Plagiorchiida trematodes, such as *Dicrocoelium chinensis*, Lancet liver fluke (*Dicrocoelium dendriticum*), African lancet fluke (*Dicrocoelium hospes*), *Eurytrema coelomaticum*, Pancreatic fluke (*Eurytrema pancreaticum*), *Paragonimus miyazakii*, *Paragonimus ohirai*, and Lung fluke (*Paragonimus westermani*).

Opisthorchiida trematodes, such as *Amphimerus* spp., Chinese liver fluke (*Clonorchis sinensis*), Cat liver fluke (*Opisthorchisfelineus*), Southeast Aasian liver fluke (*Opisthorchis viverrini*), *Pseudamphistomum* spp., *Metorchis* spp., *Parametorchis* spp., Intestinal fluke (*Heterophyes heterophyes*), *Metagonimus yokokawai*, and *Pygidiopsis summa*.

Amebas, such as *Entamoeba histolytica*, or *E. invadens*.

Piroplasmida: Sporozoa, such as *Babesia bigemina*, *Babesia bovis*, *Babesia caballi*, *Babesia canis*, *Babesia felis*, *Babesia gibsoni*, *Babesia ovata*, *Cytauxzoon felis*, *Theileria annulata*, *Theileria mutans*, *Theileria orientalis*, and *Theileria parva*.

Haemosporida: Sporozoa, such as *Haemoproteus mansoni*, *Leucocytozoon caulleryi*, *Plasmodium falciparum*, *Plasmodium malariae*, *Plasmodium ovale*, and *Plasmodium vivax*.

Eucoccidiorida: Sporozoa, such as *Caryospora* spp., *Eimeria acervulina*, *Eimeria bovis*, *Eimeria brunetti*, *Eimeria maxima*, *Eimeria necatrix*, *Eimeria ovinoidalis*, *Eimeria stiedae*, *Eimeria tenella*, *Isospora canis*, *Isospora felis*, *Isospora suis*, *Tyzzeria alleni*, *Tyzzeria anseris*, *Tyzzeria perniciosa*, *Wenyonella anatis*, *Wenyonella gagari*, *Cryptosporidium canis*, *Cryptosporidium felis*, *Cryptosporidium hominis*, *Cryptosporidium meleagridis*, *Cryptosporidium muris*, *Cryptosporidium parvum*, *Sarcocystis canis*, *Sarcocystis cruzi*, *Sarcocystis felis*, *Sarcocystis hominis*, *Sarcocystis miescheriana*, *Sarcocystis neurona*, *Sarcocystis tenella*, *Sarcocystis ovalis*, *Toxoplasma gondii*, *Hepatozoon canis*, and *Hepatozoon felis*.

Vestibuliferida: Ciliata, such as *Balantidium coli*.

Trichomonadida: Mastigophora, such as *Histomanas meleagridis*, *Pentatrichomonas hominis*, and *Trichomonas tenax*.

Diplomonadida: Mastigophora, such as *Giardia intestinalis*, *Giardia muris*, *Hexamita meleagridis*, and *Hexamita parva*.

Kinetoplastida: Mastigophora, such as *Leishmania donovani*, *Leishmania infantum*, *Leishmania major*, *Leishmania tropica*, *Trypanosoma brucei gambiense*, *Trypanosoma brucei rhodesiense*, *Trypanosoma cruzi*, *Trypanosoma equiperdum*, and *Trypanosoma evansi*. Harmful organisms in the horticulture field, and external or internal parasites of livestock, poultry, pets, or the like, which can be controlled by using the compound of the present invention, are not limited to the examples above.

Meanwhile, specific examples of the diseases will be listed below.

Diseases of konjac: Dry rot (*Fusarium oxysporum*, *F solani* f. sp. *radicicola*), Stem rot (*Athelia rolfsii*), Root rot (*Pythium aristosporum*), Bacterial leaf blight (*Acidovorax konjaci*), and Soft rot (*Erwinia carotovora* subsp. *carotovora*).

Diseases of Eddoe: Leaf mold (*Cladosporium colocasiae*), Dry rot (*Fusarium oxysporum* f sp. *colocasiae*), Black rot (*Ceratocystis* sp.), Phytophthora blight (*Phytophthora colocasiae*), *Pythium aristosporum*, *P. myriotylum*, and Bacterial soft rot (*Pectobacterium carotovorum*).

Diseases of Alliaceae crops: Leaf spot (*Heterosporium allii*), *Alternaria* leaf spot (*Alternaria porri*), Leaf spot (*Pleospora herbarum*, *Stemphylium botryosum*, *S. vesicarium*), Pink root rot (*Pyrenochaeta terrestris*, *Pyrenochaeta* sp.), Leaf blight (*Botrytis cinerea*, *B. byssoidea*, *B. squamosa*), Gray mold (*Botrytis cinerea*), Onion gray mold neck rot (*Botrytis allii*), Small sclerotial rot (*Botrytis squamosa*), Leaf blight (*Ciborinia allii*), Dry rot (*Fusarium oxysporum*), *Fusarium* basal rot (*Fusarium oxysporum* f. sp. *allii*, *F solani* f. sp. *radicicola*), Onion *fusarium* basal rot (*Fusarium oxysporum* f. sp. *cepae*), Rust (*Puccinia allii*), Smut (*Urocystis cepulae*), Allium white rot (*Sclerotium cepivorum*), Southern blight (*Athelia rolfsii*), Damping-off (*Rhizoctonia solani, Pythium* sp.), Downy mildew (*Peronospora destructor*), Phytophthora blight (*Phytophthora nicotianae*), Leaf blight (*Phytophthoraporri*), Onion soft rot (*Burkholderia cepacia*), Bacterial rot (*Pseudomonas cichorii, P. marginalis* pv. *marginalis, Erwinia* sp.), Bacterial basal bulb rot (*Pseudomonas* sp.), and Bacterial soft rot (*Pectobacterium carotovorum*).

Diseases of *asparagus*: Leaf spot (*Cercospora asparagi*), Stemphylium leaf spot (*Stemphylium botryosum*), and Stem blight (*Phomopsis asparagi*).

Diseases of Chinese yam: Brown rot (*Fusarium oxysporum, F solani* f. sp. *pisi, f.* sp. *radicicola*), Anthracnose (*Glomerella cingulata*), and Leaf spot (*Pseudophloeosporella dioscoreae*).

Diseases of rice: Stem rot (*Helminthosporium sigmoideum* var. *irregulare*), Brown spot (*Cochliobolus miyabeanus*), Seedling blight (*Phoma* sp., *Trichoderma viride, Fusarium solani, Gibberella avenacea, Mucor fragilis, Rhizopus arrhizus, R. chinensis, R. oryzae, Pythium arrhenomanes, P. graminicola, P. irregulare, P. spinosum, P. sylvaticum*), False smut (*Villosiclava virens*), "Bakanae" disease (*Gibberella fujikuroi*), Blast (*Magnaporthe grisea*), Stem rot (*Magnaporthe salvinii*), Sheath blight (*Thanatephorus cucumeris*), Bacterial grain rot (*Burkholderia gladioli, B. glumae*), Bacterial seedling blight (*Burkholderia plantarii*), Bacterial brown stripe (*Acidovorax avenae* subsp. *avenae*), Bacterial leaf blight (*Xanthomonas oryzae* pv. *oryzae*), and Bacterial palea browning (*Pantoea ananatis*).

Diseases of wheat varieties: Speckled leaf blotch (*Mycosphaerella graminicola*), Glume blotch (*Phaeosphaeria nodorum*), Spot blotch (*Cochliobolus sativus*), Barley stripe (*Pyrenophora graminea*), Barley net blotch (*Pyrenophora teres*), Barley powdery mildew (*Blumeria graminis* f. sp. *hordei*), Wheat powdery mildew (*Blumeria graminis* f. sp. *tritici*), Rye powdery mildew (*Blumeria graminis* f. sp. *secalis*), Eyespot (*Tapesia acuformis, T. yallundae*), Sclerotinia snow blight (*Sclerotinia borealis*), Ergot (*Claviceps purpurea*), Fusarium blight (*Fusarium crookwellense, F culmorum, Gibberella avenacea, G zeae*), Take-all (*Gaeumannomyces graminis*), Snow mold (*Monographella nivalis*), Cephalosporium stripe (*Cephalosporium gramineum*), Scald (*Rhynchosporium secalis*), Stem rust (*Puccinia graminis*), Barley leaf rust (*Puccinia hordei*), Brown rust (*Puccinia recondita*), Stripe rust (*Puccinia striiformis* var. *striiformis*), Flag smut (*Urocystis agropyri*), Covered smut (*Ustilago hordei*), Loose smut (*Ustilago nuda*), Bunt (*Tilletia caries, T. laevis*), Stinking smut (*Tilletia controversa*), Typhula snow blight (*Typhula incarnate, T. ishikariensis* var. *ishikariensis*), Foot-rot (*Ceratobasidium cornigerum*), Browning root rot (*Pythium graminicola, P. horinouchiense, P. iwayamai, P. okanoganense, P. paddicum, P. vanterpoolii, P. volutum*), Bacterial halo blight (*Pseudomonas syringae* pv. *coronafaciens*), and Bacterial black node (*Pseudomonas syringae* pv. *syringae*).

Diseases of grasses: Dollar spot (*Sclerotinia homoeocarpa*), Fairy rings (*Bovista dermoxantha, Conocybe apala, Lepista subnuda, Lycoperdon curtisii, L. perlatum, Marasmius oreades*), Rhizoctonia patch (*Ceratobasidium* spp.), Brown patch, Large patch (*Rhizoctonia solani*), Rust (*Puccinia zoysiae*), and Pythium blight (*Pythium graminicola, P. periplocum, P. vanterpoolii*).

Diseases of sugarcane: Leaf scorch (*Stagonospora sacchari*), Top rot (*Fusarium moniliforme* var. *majus, Gibberella fujikuroi, G fujikuroi* var. *subglutinans*), Orange rust (*Puccinia kuehnii*), Brown rust (*Puccinia melanocephala*), and Sugarcane smut (*Sporisorium scitamineum*).

Diseases of corns: Southern leaf blight (*Cochliobolus heterostrophus*), Northern leaf blight (*Setosphaeria turcica*), Seedling blight (*Gibberella avenacea, Penicillium* sp.), Southern rust (*Pucciniapolysora*), Corn smut (*Ustilago maydis*), Sheath blight (*Thanatephorus cucumeris*), and Browning root rot (*Pythium arrhenomanes, P graminicola*).

Diseases of bananas: Black sigatoka (*Mycosphaerellafijiensis*), Yellow sigatoka leaf spot (*Mycosphaerella musicola*), and Panama disease (*Fusarium oxysporum* f. sp. *cubense*).

Diseases of Zingiberaceae crops: Leaf spot (*Mycosphaerella zingiberis*), Leaf spot (*Phyllosticta zingiberis*), Blast (*Pyricularia zingiberis*), *Rhizoctonia solani*, and Root rot (*Pythium ultimum, P. zingiberis*).

Diseases of sugar beets: Cercospora leaf spot (*Cercospora beticola*), Ramularia leaf spot (*Ramularia beticola*), Leaf spot (*Pleospora betae*), Powdery mildew (*Erysiphe betae*), Leaf blight/Root rot (*Thanatephorus cucumeris*), Aphanomyces root rot (*Aphanomyces cochlioides*), and Damping-off (*Pleospora betae, Fusarium* sp., *Colletotrichum dematium, Rhizoctonia solani, Aphanomyces cochlioides, Pythium debaryanum*).

Diseases of spinach: Leaf spot (*Cercospora beticola*), Leaf mold (*Cladosporium variabile*), Fusarium wilt (*Fusarium oxysporum* f. sp. *spinaciae*), Anthracnose (*Colletotrichum dematium* f. *spinaciae*), Foot rot (*Rhizoctonia solani*), Root rot (*Aphanomyces cochlioides*), Downy mildew (*Peronospora farinosa* f. sp. *spinaciae*), Damping-off (*Pythium aphanidermatum, P. myriotylum, P. paroecandrum, P. ultimum* var. *ultimum*), and Bacterial leaf spot (*Pseudomonas syringae* pv. *spinaciae*).

Diseases of grapes: Isariopsis leaf spot (*Pseudocercospora vitis*), Anthracnose (*Elsinoe ampelina*), Powdery mildew (*Uncinula necator*), Gray mold (*Botrytis cinerea*), Swelling arm (*Diaporthe kyushuensis*), Bud blight (*Diaporthe rudis*), Dead arm (*Phomopsis viticola*), Ripe rot (*Colletotrichum acutatum, Glomerella cingulata*), Rust (*Physopella ampelopsidis*), and Downy mildew (*Plasmopara viticola*).

Diseases of Fabaceae crops: Purple stain (*Cercospora kikuchii*), Ring spot (*Cercospora zonata*), Brown Leaf spot (*Mycosphaerella arachidis*), Leaf spot (*Mycosphaerella berkeleyi*), Mycosphaerella blight (*Mycosphaerella pinodes*), Angular leaf spot (*Phaeoisariopsis griseola*), Ascochyta blight (*Ascochytapisi*), Brown spot (*Didymella fabae*), Powdery mildew (*Erysiphe pisi, Sphaerotheca fuliginea*), Gray mold (*Botrytis cinerea*), Chocolate spot (*Botrytis cinerea, B. elliptica, B. fabae*), Stem rot (*Sclerotinia sclerotiorum*), Crown and root rot (*Calonectria ilicicola*), Root rot (*Fusarium* arthrosporioides, *F. avenaceum, F. sporotrichioides*), Fusarium root-rot (*Fusarium cuneirostrum*), Fusarium wilt (*Fusarium oxysporum* f. sp. *adzukicola*), Stem wilt (*Fusarium avenaceum, F oxysporum* f. sp. *fabae*), Root rot (*Fusarium solani* f. sp. *pisi*), Anthracnose (*Colletotrichum lindemuthianum*), Anthracnose (*Colletotrichum phaseolorum*), Anthracnose (*Colletotrichum trifolii, C. truncatum, Glomerella glycines, Gloeosporium* sp.), Brown stem rot (*Phialophora gregata*), Soybean rust (*Phakopsora pachyrhizi*), Rust (*Uromyces phaseoli* var. *azukicola*), Rust (*Uromyces phaseoli* var. *phaseoli*), Rust (*Uromyces viciae-fabae* var. *viciae-fabae*), Southern blight (*Athelia rolfsii*), Downy mildew (*Peronospora manshurica*), Phytophthora root and stem rot (*Phytophthora sojae*), Phytophthora vignae f. sp. *adzukicola*, Bacterial pustule (*Xanthomonas campestris* pv. *glycines*), Bacterial blight (*Pseudomonas savastanoi* pv. *glycinea*), Halo blight (*Pseudomonas savastanoi* pv. *phaseolicola*), and *Pseudomonas syringae* pv. *syringae*.

Diseases of hops: Powdery mildew (*Oidium sp., Sphaerotheca intermedia*), Gray mold (*Botrytis cinerea*), Hop wilt (*Verticillium albo-atrum*), and Downy mildew (*Pseudoperonospora humuli*).

Diseases of fig trees: Souring (*Candida* sorbosa, *Candida* sp., *Pichia kluyveri*), Fig scab (*Sphaceloma caricae*), Gray mold (*Botrytis cinerea*), Ceratocystis canker (*Ceratocystis fimbriata*), White root rot (*Rosellinia necatrix*), Anthracnose (*Glomerella cingulata*), Rust (*Phakopsora nishidana*), Rhizopus rot (*Rhizopus stolonifer* var. *stolonifer*), and White powdery rot (*Phytophthora palmivora*).

Diseases of mulberries: Powdery mildew (*Phyllactinia moricola*), Twig blight (*Hypomyces solani* f. sp. *mori*, f. sp. *pisi*, *Gibberella baccata*), Dieback (*Diaporthe nomurai*), White root rot (*Rosellinia necatrix*), Violet root rot (*Helicobasidium longisporum*), Red rust (*Aecidium mori*), Bacterial blight (*Pseudomonas syringae* pv. *mori*), and Shoot soft rot (*Pectobacterium carotovorum*).

Diseases of roses: Stem canker (*Leptosphaeria coniothyrium*), Powdery mildew (*Podosphaerapannosa, Uncinuliella simulans*), Black spot (*Diplocarpon rosae*), Botrytis blight (*Botrytis cinerea*), Rust (*Kuehneola japonica, Phragmidium fusiforme, P. mucronatum, P. rosae-multiflorae*), Downy mildew (*Peronospora sparsa*), and Crown gall (*Agrobacterium tumefaciens*).

Diseases of strawberries: Leaf spot (*Mycosphaerella fragariae*), Powdery mildew (*Sphaerotheca aphanis* var. *aphanis*), Gray mold (*Botrytis cinerea*), Fusarium wilt (*Fusarium oxysporum* f. sp. *fragariae*), Leaf blight (*Phomopsis obscurans*), Crown rot (*Colletotrichum acutatum, C. fragariae, Glomerella cingulata*), Phytophthora rot (*Phytophthora cactorum, P. nicotianae, Phytophthora* sp.), and Red stele (*Phytophthora fragariae*).

Diseases of loquats: Entomosporium leaf spot (*Diplocarpon mespili*), Gray leaf spot (*Pestalotia eriobotrifolia, Pestalotiopsis funereal, P. neglecta*), White root rot (*Rosellinia necatrix*), Anthracnose (*Colletotrichum acutatum, Glomerella cingulata*), and Canker (*Pseudomonas syringae* pv. *eriobotryae*).

Diseases of apples: Fruit spot (*Mycosphaerella pomi*), Alternaria blotch (*Alternaria mali*), Scab (*Venturia Inaequalis*), Ring rot (*Botryosphaeria berengeriana* f. sp. *piricola*), Fly speck (*Schizothyrium pomi*), Powdery mildew (*Podosphaera leucotricha*), Blotch (*Diplocarpon mali*), Blossom blight (*Monilinia mali*), Valsa canker (*Valsa ceratosperma*), White root rot (*Rosellinia necatrix*), Bitter rot (*Colletotrichum acutatum, Glomerella cingulata*), Sooty blotch (*Phyllachora pomigena*), Violet root rot (*Helicobasidium longisporum*), Rust (*Gymnosporangium yamadae*), and Fire blight (*Erwinia amylovora*).

Diseases of nashi pears: Black spot (*Alternaria kikuchiana*), Brown spot (*Stemphylium* sp.), Scab (*Venturia nashicola*), Ring rot (*Botryosphaeria berengeriana* f. sp. *piricola*), Shoot blight (*Botryosphaeria dothidea*), Powdery mildew (*Phyllactinia mali*), Phomopsis canker (*Phomopsis fukushii*), Coral spot (*Nectria cinnabarina*), White root rot (*Rosellinia necatrix*), Anthracnose (*Colletotrichum acutatum, Glomerella cingulata*), Rust (*Gymnosporangium asiaticum*), Phytophthora fruit rot (*Phytophthora cactorum, P. syringae*), Bacterial black spot (*Pseudomonas syringae* pv. *syringae*), and Fire blight (*Erwinia amylovora*).

Diseases of apricots: Scab (*Venturia carpophila*), Zonate leaf spot (*Grovesinia pruni*), Brown rot (*Monilinia fructicola, M. fructigena, M. laxa*), Shoot blight (*Coryneum* sp.), Anthracnose (*Gloeosporium sp., Colletotrichum acutatum*), and Bacterial shot hole (*Xanthomonas campestris* pv. *pruni*).

Diseases of Japanese apricots: Scab (*Venturia carpophila*), Gray mold (*Botrytis cinerea*), Zonate leaf spot (*Grovesinia pruni*), Brown rot (*Monilia mumecola, Monilinia fructicola, M. laxa*), Anthracnose (*Colletotrichum acutatum, Glomerella cingulata*), Sooty blotch (*Peltaster* sp.), Chloranthy (*Blastospora smilacis*), and Bacterial canker (*Pseudomonas syringae* pv. *morsprunorum, Erwinia* sp.).

Diseases of Japanese plums: Plum pockets (*Taphrinapruni*), Brown rot (*Monilinia fructicola, M. fructigena*), Anthracnose (*Colletotrichum acutatum*), and Bacterial leaf spot (*Xanthomonas arboricola* pv. *pruni*).

Diseases of peaches: Leaf curl (*Taphrina deformans*), Scab (*Venturia carpophila*), Blister canker (*Botryosphaeria berengeriana f. sp. perscicae*), Powdery mildew (*Podosphaerapannosa, P. tridactyla* var. *tridactyla*), Brown rot (*Monilinia fructicola, M. fructigena*), Phomopsis rot (*Phomopsis* sp.), Cytospora canker (*Leucostoma persoonii*), Anthracnose (*Colletotrichum acutatum, Glomerella cingulata*), Fruit red spot (*Ellisembia* sp.), Brown rust (*Tranzschelia discolor*), and Bacterial shot hole (*Xanthomonas arboricola* pv. *pruni, Pseudomonas syringae* pv. *syringae, Brenneria nigrifluens*).

Diseases of cherries: Cylindrosporium leaf spot (*Mycosphaerella cerasella, Blumeriella jaapii*), Brown rot (*Monilinia fructicola, M. fructigena, M. laxa*), Young-fruit rot (*Monilinia kusanoi*), White root rot (*Rosellinia necatrix*), Anthracnose (*Colletotrichum acutatum, Glomerella cingulata*), Rhizopus rot (*Rhizopus stolonifer* var. *stolonifer*), and Bacterial canker (*Pseudomonas syringae, P. s.* pv. *syringae, P. viridiflava*).

Diseases of pepos: Scab (*Cladosporium cucumerinum*), Corynespora leaf spot (*Corynespora cassiicola*), Gummy stem blight (*Didymella bryoniae*), Powdery mildew (*Erysiphe betae, Leveillula taurica, Oidium* sp., *Podosphaera xanthii, Sphaerotheca fuliginea*), Gray mold (*Botrytis cinerea*), Sclerotinia rot (*Sclerotinia sclerotiorum*), Fusarium wilt (*Fusarium oxysporum* f. sp. *cucumerinum*, f. sp. *lagenariae*, f. sp. *luffae*, f. sp. *melonis*, *f.* sp. *niveum*), Fusarium basal rot (*Fusarium solani* f. sp. *cucurbitae*), Phomopsis sp., Root rot (*Monosporascus cannonballus*), Plectosporium blight (*Monographella cucumerina*), Anthracnose (*Colletotrichum orbiculare, Glomerella cingulata*), Southern blight (*Athelia rolfsii*), Damping-off (*Rhizoctonia solani, Pythium cucurbitacearum, P. debaryanum, P. spinosum*), Downy mildew (*Pseudoperonospora cubensis*), Brown rot (*Phytophthora capsici*), Phytophthora rot (*Phytophthora capsici, P. cryptogea, P. melonis, P. nicotianae*), Pythium fruit rot (*Pythium aphanidermatum*), Bacterial fruit blotch (*Acidovorax avenae* subsp. *citrulli*), Bacterial spot (*Xanthomonas campestris* pv. *cucurbitae*), Marginal blight (*Pseudomonas marginalis* pv. *marginalis, P. viridiflava*), and Angular leaf spot (*Pseudomonas syringae* pv. *lachrymans*).

Diseases of Japanese chestnuts: Endothia canker (*Cryphonectria parasitica*) and Anthracnose (*Glomerella cingulata*).

Diseases of Brassicaceae vegetables: White spot (*Pseudocercosporella capsellae*), Black leg (*Leptosphaeria maculans*), Alternaria leaf spot (*Alternaria brassicae, A. brassicicola, A. japonica*), Alternaria sooty spot (*Alternaria brassicicola*), Black leg (*Phoma wasabiae*), Gray mold (*Botrytis cinerea*), Snow mold (*Sclerotinia nivalis, Typhula japonica, T. incarnate, T. ishikariensis* var. *ishikariensis*), Sclerotinia rot (*Sclerotinia sclerotiorum*), Yellows (*Fusarium oxysporum* f. sp. *conglutinans*), Yellows (*Fusarium oxysporum* f. sp. *raphani*), *Verticillium* black spot (*Verticillium albo-atrum, V. dahliae*), Yellows (*Verticillium dahliae*), *Verticillium* wilt (*Verticillium longisporum*), Anthracnose (*Colletotrichum dematium, C. destructivum, C. higginsianum*), Damping-off (*Rhizoctonia solani*), Club root (*Plasmodiophora brassicae*), White rust (*Albugo macrospora*), White rust (*Albugo wasabiae*), Downy mildew (*Hyaloperonospora brassicae*), Downy mildew (*Peronospora alliariae-wasabi*), Downy mildew (*Peronospora parasitica*), Damping-off (*Pythium buismaniae, P. zingiberis, Rhizoctonia solani*), Damping-off (*Pythium* sp.), Black rot (*Xanthomonas campestris* pv. *campestris*), Head rot (*Pseudomonas fluorescens, P. viridiflava, Pectobacterium carotovorum*), Bacterial black spot (*Pseudomonas syringae* pv. *maculicola*), and Bacterial soft rot (*Pectobacterium carotovorum, P. wasabiae*).

Diseases of papayas: *Phytophthora* blight (*Phytophthora nicotianae*).

Diseases of okras: Brown leaf mold (*Pseudocercospora abelmoschi*), *Alternaria* rot (*Alternaria alternata*), Pod spot (*Phoma exigua* var. *exigua*), Powdery mildew (*Leveillula taurica*), Gray mold (*Botrytis cinerea*), Black root rot (*Thielaviopsis basicola*), Damping-off (*Rhizoctonia solani, Pythium ultimum* var. *ultimum, Pythium* sp.), and *Pseudomonas cichorii, P. viridiflava*.

Diseases of mangos: Anthracnose (*Colletotrichum acutatum, Glomerella cingulata*).

Diseases of citruses: Greasy spot (*Mycosphaerella citri, M. horii*), Scab (*Elsinoefawcettii*), Black rot (*Alternaria citri*), Common green mold (*Penicillium digitatum*), Blue mold (*Penicillium italicum*), Gray mold (*Botrytis cinerea*), Melanose (*Diaporthe citri*), Melanose like blemish (*Alternaria citri, Diaporthe rudis*), White root rot (*Rosellinia necatrix*), Anthracnose (*Glomerella cingulata*), Brown rot (*Phytophthora citricola, P. citrophthora, P. nicotianae, P. palmivora*), and *Citrus* canker (*Xanthomonas citri* subsp. *citri*).

Diseases of kiwifruits: Sooty spot (*Pseudocercospora actinidiae*), Soft rot (*Botryosphaeria dothidea, Lasiodiplodia theobromae, Diaporthe* sp.), Gray mold (*Botrytis cinerea*), White root rot (*Rosellinia necatrix*), Anthracnose (*Colletotrichum acutatum, Glomerella cingulata*), Bacterial blossom blight (*Pseudomonas marginalis* pv. *marginalis, P. syringae* pv. *syringae, P. viridiflava*), and Bacterial canker (*Pseudomonas syringae* pv. *actinidiae*).

Diseases of *kaki* persimmons: Angular leaf spot (*Cercospora kaki*), Circular leaf spot (*Mycosphaerella nawae*), Black spot (*Fusicladium levieri*), Fly speck (*Schizothyrium pomi*), Powdery mildew (*Phyllactinia kakicola*), Gray mold (*Botrytis cinerea*), Black leaf spot (*Discostroma* sp.), and Anthracnose (*Glomerella cingulata*).

Diseases of blueberries: Gray mold (*Botrytis cinerea*) and *Valdensia* leaf blight (*Valdensia heterodoxa*).

Diseases of tea plants: Brown round spot (*Cercospora chaae, Pseudocercospora ocellata*), Anthracnose (*Discula theae-sinensis*), Gray blight (*Pestalotiopsis longiseta, P. theae*), White root rot (*Rosellinia necatrix*), Brown blight (*Glomerella cingulata*), Net blister blight (*Exobasidium reticulatum*), Blister blight (*Exobasidium vexans*), Black rot (*Ceratobasidium* sp.), and Bacterial shoot blight (*Pseudomonas syringae* pv. *theae*).

Diseases of shiso: *Corynespora* leaf spot (*Corynespora cassiicola*) and Rust (*Coleosporium plectranthi*).

Diseases of sesame: Stem rot (*Athelia rolfsii*), Bacterial wilt (*Ralstonia solanacearum*), and Bacterial leaf spots (*Pseudomonas syringae* pv. *sesami*).

Diseases of sweet potatoes: Stem rot (*Fusarium oxysporum* f. sp. *batatas, F solani*), Black rot (*Ceratocystisfimbriata*), Violet root rot (*Helicobasidium longisporum*), Soft rot (*Rhizopus stolonifer* var. *stolonifer, R. tritici*), and Soil rot (*Streptomyces ipomoeae*).

Diseases of tomatoes: Leaf mold (*Mycovellosiella fulva*), *Cercospora* leaf mold (*Pseudocercospora fuligena*), *Corynespora* target spot (*Corynespora cassiicola*), Early blight (*Alternaria solani*), Leaf spot (*Stemphylium lycopersici, S. solani*), Brown root rot (*Pyrenochaeta lycopersici*), Powdery mildew (*Leveillula taurica, Oidium neolycopersici, Oidium* sp.), Gray mold (*Botrytis cinerea*), Stem rot (*Sclerotinia sclerotiorum*), *Fusarium* wilt (*Fusarium oxysporum* f. sp. *lycopersici*), Crown and root rot (*Fusarium oxysporum* f. sp. *radicis-lycopersici*), *Verticillium* wilt (*Verticillium dahliae*), Southern blight (*Athelia rolfsii*), Damping-off (*Rhizoctonia solani, Pythium vexans*), Late blight (*Phytophthora infestans*), Bacterial canker (*Clavibacter michiganensis* subsp. *michiganensis*), Bacterial wilt (*Ralstonia solanacearum*), Bacterial spot (*Xanthomonas campestris* pv. *vesicatoria*), and Bacterial soft rot (*Pectobacterium carotovorum*).

Diseases of eggplants: Leaf mold (*Mycovellosiella nattrassii*), Leaf spot (*Paracercospora egenula*), Black blight (*Corynespora cassiicola*), Early blight (*Alternaria solani*), Powdery mildew (*Erysiphe cichoracearum, Leveillula taurica, Sphaerotheca fuliginea*), Gray mold (*Botrytis cinerea*), Stem rot (*Sclerotinia sclerotiorum*), *Fusarium oxysporum* f. sp. *melongenae, Verticillium* wilt (*Verticillium dahliae*), Brown spot (*Phomopsis vexans*), Southern blight (*Athelia rolfsii*), Damping-off (*Rhizoctonia solani*), Brown rot (*Phytophthora capsici*), Late blight (*Phytophthora infestans*), Bacterial wilt (*Ralstonia solanacearum*), and Necrotic leaf spot (*Pseudomonas cichorii*).

Diseases of potatoes: Early blight (*Alternaria solani*), Dry rot (*Fusarium oxysporum, Fusarium solani* f. sp. *eumartii, f.* sp. *radicicola*), Anthracnose (*Colletotrichum coccodes*), Black scurf (*Thanatephorus cucumeris*), Powdery Scab (*Spongospora subterranea* f. sp. *subterranea*), Late blight (*Phytophthora infestans*), Ring rot (*Clavibacter michiganensis* subsp. *Sepedonicus*), Scab (*Streptomyces* spp.), Bacterial wilt (*Ralstonia solanacearum*), Black leg (*Dickeya dianthicola, Pectobacterium atrosepticum, P. carotovorum*), and Bacterial soft rot (*Pectobacterium carotovorum*).

Diseases of chili peppers and bell peppers: Frogeye leaf spot (*Cercospora capsici*), *Corynespora* blight (*Corynespora cassiicola*), Stemphyrium leaf spot (*Stemphylium lycopersici*), Powdery mildew (*Leveillula taurica*), Gray mold (*Botrytis cinerea*), *Sclerotinia* rot (*Sclerotinia sclerotiorum*), *Fusarium* wilt (*Fusarium oxysporum*), Anthracnose (*Colletotrichum acutatum, C. capsici, C. nigrum*), Southern blight (*Athelia rolfsii*), Damping-off (*Rhizoctonia solani*), *Phytophthora* blight (*Phytophthora capsici*), Bacterial wilt (*Ralstonia solanacearum*), Bacterial spot (*Xanthomonas campestris* pv. *vesicatoria*), and Bacterial soft rot (*Pectobacterium carotovorum*).

Diseases of tobaccos: Brown spot (*Alternaria alternata*), Sore shin (*Rhizoctonia solani*), Black shank (*Phytophthora nicotianae*), and Bacterial wilt (*Ralstonia solanacearum*).

Diseases of celery: Early blight (*Cercospora apii*), Late blight (*Septoria apiicola*), and Bacterial soft rot (*Pectobacterium carotovorum*).

Diseases of Japanese honeywort: *Sclerotinia* rot (*Sclerotinia sclerotiorum*), *Fusarium oxysporum* f. sp. *apii*, Rust (*Puccinia tokyensis*), *Rhizoctonia solani*, Downy mildew (*Plasmopara nivea*), and *Pythium aphanidermatum, P. apleroticum, Pythium* sp.

Diseases of carrots: Cercospora blight (*Cercospora carotae*), Leaf blight (*Alternaria dauci*), *Alternaria* black rot (*Alternaria radicina*), Powdery mildew (*Erysiphe heraclei*), Sclerotinia rot (*Sclerotinia minor, S. sclerotiorum*), Dry rot (*Fusarium solani* f. sp. *radicicola, Gibberella avenacea*), Violet root rot (*Helicobasidium longisporum*), Southern blight (*Athelia rolfsii*), Southern blight (*Athelia rolfsii*), Damping-off (*Rhizoctonia solani*), Brown blotted root rot (*Pythium sulcatum*), Crown gall (*Agrobacterium tumefaciens*), and Bacterial soft rot (*Pectobacterium carotovorum*).

Diseases of parsley: Leaf spot (*Cercospora apii*), Powdery mildew (*Erysiphe heraclei*), *Phytophthora nicotianae*, and Bacterial soft rot (*Pectobacterium carotovorum*).

Diseases of *Aralia elata*: Spot anthracnose (*Elsinoe araliae*) and *Phytophthora cactorum*.

Diseases of udos: Leaf spot (*Alternariapanax, Alternaria* sp.), Sclerotinia rot (*Sclerotinia sclerotiorum*), Verticillium wilt (*Verticillium dahliae*, V *nigrescens*), Southern blight (*Athelia rolfsii*), and Phytophthora rot (*Phytophthora cactorum*).

Diseases of lettuce: Gray mold (*Botrytis cinerea*), Stem rot (*Sclerotinia sclerotiorum*), Root rot (*Fusarium oxysporum* f. sp. *lactucae*), Bottom rot (*Rhizoctonia solani*), Downy mildew (*Bremia lactucae*), Bacterial spot (*Xanthomonas axonopodis* pv. *vitians*), Bacterial rot (*Pseudomonas cichorii, P. marginalis* pv. *Marginalis, P. viridiflava*), and Bacterial soft rot (*Pectobacterium carotovorum*).

Diseases of *Chrysanthemum morifolium*: Leaf spot (*Septoria chrysanthemella*), Leaf blight (*Septoria obesa*), Ray blight (*Didymella chrysanthemi*), Powdery mildew (*Erysiphe cichoracearum* var. *cichoracearum*), Botrytis blight (*Botrytis cinerea*), Stem rot (*Sclerotinia sclerotiorum*), Wilt (*Verticillium dahliae*), Rust (*Phakopsora artemisiae*), Rust (*Puccinia horiana*), Rust (*Puccinia tanaceti* var. *tanaceti*), Petal blight (*Itersonilia perplexans*), Southern blight (*Athelia rolfsii*), Root and stem rot (*Ceratobasidium cornigerum, Rhizoctonia solani*), Downy mildew (*Peronospora danica*), Phytophthora rot (*Phytophthora cactorum, Phytophthora* sp.), Crown gall (*Agrobacterium tumefaciens*), Bacterial wilt (*Ralstonia solanacearum*), and Bacterial stem rot (*Pectobacterium carotovorum*).

Diseases of crown daisies: Leaf blight (*Cercospora chrysanthemi*), Anthracnose (*Colletotrichum acutatum*), and Downy mildew (*Peronospora chrysanthemi-coronarii*).

Diseases of sunflowers: Leaf spot (*Septoria helianthi*), Leaf spot (*Alternaria helianthi*), Powdery mildew (*Erysiphe cichoracearum, Golovinomyces cichoracearum* var. *latisporus, Oidium* sp., *Podosphaerafusca*), Gray mold (*Botrytis cinerea*), Sclerotinia rot (*Sclerotinia sclerotiorum*), Root and stem rot (*Rhizoctonia solani*), Downy mildew (*Plasmopara halstedii*), Bacterial leaf spot (*Pseudomonas syringae* pv. *helianthi*), and *Pectobacterium carotovorum*.

Diseases of fuki: Verticillium wilt (*Verticillium dahliae*) and Southern blight (*Athelia rolfsii*).

Diseases of burdocks: Leaf spot (*Phoma exigua* var. *exigua*), Powdery mildew (*Podosphaerafusca*), Black streak (*Itersonilia perplexans*), Black scurf (*Rhizoctonia solani*), *Pythium irregulare*, and Bacterial spot (*Xanthomonas campestris* pv. *nigromaculans*). Diseases of plants, which can be controlled by using the compound of the present invention, are not limited to the examples above.

Compound (1) and a composition of the present invention containing Compound (1) are useful for controlling Stink bugs, Hemiptera Pentatomidae, which have been problematic in soybean fields in recent years, or are useful for controlling weevils, Curculionidae Family, which have been problematic in cotton fields.

Also, Compound (2) and a composition of the present invention containing Compound (2) are useful for controlling Stink bugs, Hemiptera Pentatomidae, which have been problematic in soybean fields in recent years, or are useful for controlling weevils, Curculionidae Family, which have been problematic in cotton fields.

Compound (1) and the composition of the present invention containing Compound (1) are useful for controlling pests parasitic to honey bees, which have been problematic in recent years.

Also, Compound (2) and the composition of the present invention containing Compound (2) are useful for controlling pests parasitic to honey bees, which have been problematic in recent years.

Examples of the pest parasitic to honey bees include honeybee microsporidia (*Nosema apis*), *Varroa* mite, *Acarapis woodi, Aethina tumida, Achroia innotata obscurevittella*, and *Galleria mellonella* (wax moth larvae). Among them, *Varroa* mite, *Tropilaelaps clareae*, and *Acarapis woodi* are preferred.

Examples of the honey bees include bumble bees, stingless bees, *Apis dorsata, Apis laboriosa, Apis florea, Apis andreniformis, Apis mellifera, Apis cerana*, and *Apis koschevnikovi*. Among them, *Apis mellifera* and *Apis cerana* are preferred. The honey bees refer to all members in the population, including workers, drones, eggs, larvae, pupae, and queen.

That is, the composition of the present invention and the method of the present invention are extremely effective to harmful organisms that are resistant to conventional insecticides, such as organophosphorus compounds, carbamate compounds and pyrethroid compounds; and harmful organisms belonging to insects of Coleoptera, Hymenoptera, Lepidoptera, Diptera, Siphonaptera, Thysanoptera, Hemiptera, Psocodea (Mallophage and Anoplura), Orthoptera, Dictyoptera, Isoptera, Collembola, or the like; crustaceans of Isopoda or the like; mites of Astigmata (Acaridae, Analgidae, Psoroptidae, and Sarcoptidae), Prostigmata (Cheyletidae, Demodicidae, Eriophyidae, Tarsonemidae, Tetranychidae, Penthaleidae, and Trombiculidae), Metastigmata (Argasidae and Ixodidae), Mesostigmata (Dermanyssidae, Macronyssidae, and Varroidae), or the like; Gastropoda; and nematodes of Trichocephalida, Rhabditida, Strongylida, Aphelenchida, Tylenchida, Ascaridida, Camallanida, Oxyurida, Spirurida, or the like; can effectively be controlled with low concentrations. Meanwhile, the composition of the present invention and the method of the present invention have extremely little adverse effects to mammals, fishes, crustaceans, and beneficial insects (useful insects, such as honey bees and bumble Bees; and natural enemy insects, such as Aphelinidae, Aphidiidae, Tachinidae, and Orius), and thus have useful characteristics.

When the first active ingredient compound I and the second active ingredient compound II shown in Table 1 are combined in the composition of the present invention, the composition of the present invention and the method of the present invention provide excellent synergistic effects, particularly to mites and Hemiptera pests. The synergistic effects are more prominent to spider mites, such as *Panonychus citri, Tetranychus urticae*, and *Tetranychus kanzawai* among the mites; and to aphids and whiteflies among the Hemiptera pests.

The "plants" herein refers to Tracheophyta, such as grain, fruits, and vegetables, which are cultivated as food of humans; forage crops for livestock, poultry, and the like; ornamental plants for cherishing their appearances; and plantings at parks, streets, and the like. Specific examples include the plants listed below, but not limited thereto.

Pinales plants such as Japanese Red Pine (*Pinus densiflora*), Scots Pine (*Pinus sylvestris*), and Japanese Black Pine (*Pinus thunbergii*) belonging to Pinaceae or the like.

Magnoliids such as Pepper (*Piper nigrum*) belonging to Piperaceae; Avocado (*Persea americana*) belonging to Lauraceae; or the like.

Monocots such as Konjac (*Amorphophallus konjac*) and Eddoe (*Colocasia esculenta*) belonging to Araceae; Chinese yam (*Dioscorea batatas*) and Japanese yam (*Dioscorea japonica*) belonging to Dioscoreaceae; Leek (*Allium ampeloprasum* var. *porrum*), Onion (*Allium cepa*), Rakkyo (*Allium chinense*), Welsh onion (*Allium fistulosum*), Garlic (*Allium sativum*), Chives (*Allium schoenoprasum*), Chive (*Allium schoenoprasum* var. *foliosum*), Oriental garlic (*Allium tuberosum*), and Scallion (*Allium x wakegi*) belonging to Alliaceae; Asparagus (*Asparagus officinalis*) belonging to Asparagaceae; Coconut palm (*Cocos nucifera*) and Oil palm (*Elaeis guineensis*) belonging to Arecoideae of Arecaceae; Date palm (*Phoenix dactylifera*) belonging to Coryphoideae of Arecaceae; Pineapple (*Ananas comosus*) belonging to Bromeliaceae; Rice (*Oryza sativa*) belonging to Ehrhartoideae of Poaceae; Bent grass (*Agrostis* spp.), Blue grass (*Poa* spp.), Barley (*Hordeum vulgare*), Wheat (*Triticum aestivum, T. durum*), and Rye (*Secale cereale*) belonging to Pooideae of Poaceae; Bermuda grass (*Cynodon dactylon*) and Grass (*Zoysia* spp.) belonging to Chloridoideae of Poaceae; Sugarcane (*Saccharum officinarum*), Sorgum (*Sorghum bicolor*), and Corn (*Zea mays*) belonging to Panicoideae of Poaceae; Banana (*Musa* spp.) belonging to Musaceae; Myoga (*Zingiber mioga*) and Ginger (*Zingiber officinale*) belonging to Zingiberaceae; or the like.

Eudicots such as Lotus root (*Nelumbo nucifera*) belonging to Nelumbonaceae; Peanut (*Arachis hypogaea*), Chickpea (*Cicer arietinum*), Lentil (*Lens culinaris*), Pea (*Pisum sativum*), Broad bean (*Vicia faba*), Soybean (*Glycine max*), Common bean (*Phaseolus vulgaris*), Adzuki bean (*Vigna angularis*), and Cowpea (*Vigna unguiculata*) belonging to Fabaceae; Hop (*Humulus lupulus*) belonging to Cannabaceae; Fig Tree (*Ficus carica*) and Mulberry (*Morus* spp.) belonging to Moraceae; Common jujube (*Ziziphus jujuba*) belonging to Rhamnaceae; Strawberry (*Fragaria*) and Rose (*Rosa* spp.) belonging to Rosoideae of Rosaceae; Japanese loquat (*Eriobotrya japonica*), Apple (*Malus pumila*), European Pear (*Pyrus communis*), and Nashi Pear (*Pyrus pyrifolia* var. *culta*) belonging to Maloideae of Rosaceae; Peach (*Amygdalus persica*), Apricot (*Prunus armeniaca*), Cherry (*Prunus avium*), Prune (*Prunus domestica*), Almond (*Prunus dulcis*), Japanese Apricot (*Prunus mume*), Japanese Plum (*Prunus salicina*), *Cerasus speciosa*, and *Cerasus x yedoensis* 'Somei-yoshino' belonging to Prunoideae of Rosaceae; Winter melon (*Benincasa hispida*), Watermelon (*Citrullus lanatus*), Bottle gourd (*Lagenaria siceraria* var. *hispida*), Luffa (*Luffa cylindrica*), Pumpkin (*Cucurbita* spp.), Zucchini (*Cucurbita pepo*), Bitter melon (*Momordica charantia* var. *pavel*), Muskmelon (*Cucumis melo*), Oriental pickling melon (*Cucumis melo* var. *conomon*), Oriental melon (*Cucumis melo* var. *makuwa*), and Cucumber (*Cucumis sativus*) belonging to Cucurbitaceae; Japanese Chestnut (*Castanea crenata*) belonging to Fagaceae; Walnut (*Juglans* spp.) belonging to Juglandaceae; Cashew (*Anacardium occidentale*), Mango (*Mangifera indica*), and Pistachio (*Pistacia vera*) such as Anacardiaceae; Japanese pepper (*Zanthoxylum piperitum*) belonging to Rutoideae of Rutaceae; Bitter orange (*Citrus aurantium*), Lime (*Citrus aurantifolia*), Hassaku orange (*Citrus hassaku*), Yuzu (*Citrus junos*), Lemon (*Citrus limon*), Natsumikan (*Citrus natsudaidai*), Grapefruit (*Citrus* x *paradisi*), Orange (*Citrus sinensis*), Kabosu (*Citrus sphaerocarpa*), Sudachi (*Citrus sudachi*), Mandarin Orange (*Citrus tangerina*), Satsuma (*Citrus unshiu*), and Kumquat (*Fortunella* spp.) belonging to Aurantioideae of Rutaceae; Horseradish (*Armoracia rusticana*), Mustard (*Brassica juncea*), Takana (*Brassica juncea* var. *integrifolia*), Rapeseed (*Brassica napus*), Cauliflower (*Brassica oleracea* var. *botrytis*), Cabbage (*Brassica oleracea* var. *capitata*), Brussels sprout (*Brassica oleracea* var. *gemmifera*), Broccoli (*Brassica oleracea* var. *italica*), Green pak choi (*Brassica rapa* var. *chinensis*), Nozawana (*Brassica rapa* var. *hakabura*), Napa cabbage (*Brassica rapa* var. *nippo-oleifera*), Potherb Mustard (*Brassica rapa* var. *nipposinica*), Napa cabbage (*Brassica rapa* var. *pekinensis*), Turnip leaf (*Brassica rapa* var. *perviridis*), Turnip (*Brassica rapa* var. *rapa*), Garden rocket (*Eruca vesicaria*), Daikon (*Raphanus sativus* var. *longipinnatus*), and Wasabi (*Wasabia japonica*) belonging to Brassicaceae; Papaya (*Carica papaya*) belonging to Caricaceae; Okra (*Abelmoschus esculentus*), Cotton plant (*Gossypium* spp.), and Cacao (*Theobroma cacao*) belonging to Malvaceae; Grape (*Vitis* spp.) belonging to Vitaceae; Sugar beet (*Beta vulgaris* ssp. *vulgaris* var. *altissima*), Table beet (*Beta vulgaris* ssp. *vulgaris* var. *vulgaris*), and Spinach (*Spinacia oleracea*) belonging to Amaranthaceae; Buckwheat (*Fagopyrum esculentum*) belonging to Polygonaceae; Kaki Persimmon (*Diospyros kaki*) belonging to Ebenaceae; Tea plant (*Camellia sinensis*) belonging to Theaceae; Kiwifruit (*Actinidia deliciosa, A. chinensis*) belonging to Actinidiaceae; Blueberry (*Vaccinium* spp.) and Cranberry (*Vaccinium* spp.) belonging to Ericaceae; Coffee plants (*Coffea* spp.) belonging to Rubiaceae; Lemon balm (*Melissa officinalis*), Mint (*Mentha* spp.), Basil (*Ocimum basilicum*), Shiso (*Perilla frutescens* var. *crispa*), *Perilla frutescens* var. *frutescens*, Common Sage (*Salvia officinalis*), and Thyme (*Thymus* spp.) belonging to Lamiaceae; Sesame (*Sesamum indicum*) belonging to Pedaliaceae; Olive (*Olea europaea*) belonging to Oleaceae; Sweet potato (*Ipomoea batatas*) belonging to Convolvulaceae; Tomato (*Solanum lycopersicum*), Eggplant (*Solanum melongena*), Potato (*Solanum tuberosum*), Chili pepper (*Capsicum annuum*), Bell pepper (*Capsicum annuum* var. 'grossum'), and Tobacco (*Nicotiana tabacum*) belonging to Solanaceae; Celery (*Apium graveolens* var. *dulce*), Coriander (*Coriandrum sativum*), Japanese honeywort (*Cryptotaenia Canadensis* subsp. *japonica*), Carrot (*Daucus carota* subsp. *sativus*), Parsley (*Petroselium crispum*), and Italian parsley (*Petroselinum neapolitanum*) belonging to Apiaceae; Udo (*Aralia cordata*) and *Aralia elata* belonging to Araliaceae; Artichoke (*Cynara scolymus*) belonging to Carduoideae Asteraceae; Chicory (*Cichorium intybus*) and Lettuce (*Lactuca sativa*) belonging to Asteraceae of Asteraceae; Florists' daisy (*Dendranthema grandiflorum*), Crown daisy (*Glebionis coronaria*), Sunflower (*Helianthus annuus*), Fuki (*Petasites japonicus*), and Burdock (*Arctium lappa*) belonging to Asteraceae of Asteraceae; or the like.

The "plants" herein also refers to plants that have acquired tolerance to HPPD inhibitors, such as isoxaflutole; ALS inhibitors, such as imazethapyr and thifensulfuronmethyl; EPSP synthetase inhibitors, such as glyphosate; glutamine synthetase inhibitors, such as glufosinate; acetyl CoA carboxylase inhibitors, such as sethoxydim; PPO inhibitors, such as flumioxazin; and herbicides, such as bromoxynil, dicamba, and 2,4-D; by classical breeding methods and gene recombinant technologies.

Examples of the "horticultural plants" that have acquired tolerance by classical breeding methods include the rapeseed, wheat, sunflower, rice, and corn, which are tolerant to ALS-inhibitory imidazolinone herbicides, such as imazethapyr. Such plants are already commercially available with the product name of Clearfield <registered trademark>.

Also, the soybean that has acquired tolerance to ALS-inhibitory sulfonylurea herbicides, such as thifensulfuron-methyl, by a classical breeding method is already commercially available with the product name of STS soybean. In addition, examples of horticultural plants that have acquired tolerance to acetyl CoA carboxylase inhibitors, such as trione oxime herbicide and aryloxyphenoxypropionate herbicides, by classical breeding methods include the SR corn. The horticultural plants that have acquired tolerance to acetyl CoA carboxylase inhibitors are described in Proc. Natl. Acad. Sci. USA, volume 87, pages 7,175 to 7,179 (1990) and the like. Meanwhile, the mutant acetyl CoA carboxylases that are tolerant to acetyl CoA carboxylase inhibitors are reported in Weed Science, volume 53, pages 728 to 746 (2005) and the like. Plants tolerant to acetyl CoA carboxylase inhibitors can be produced by introducing these mutant acetyl CoA carboxylase genes into plants by gene recombinant technologies, or by introducing mutations related to acquisition of the tolerance into acetyl CoA carboxylases of crops. Moreover, plants resistant to acetyl CoA carboxylase inhibitors/herbicides can be produced by introducing nucleic acids inducing base-substituted mutants, which are exemplified by the chimeraplasty technique (Gura T. 1999. Repairing the Genome's Spelling Mistakes. Science 285: 316-318), into plant cells, so that site-specific amino acid substitution mutations are induced in acetyl CoA carboxylase/herbicide-targeted genes of crops.

Examples of the horticultural plants that have acquired tolerance by gene recombinant technologies include glyphosate-tolerant varieties of corn, soybean, cotton, rapeseed, and sugar beet, and they are already commercially available with the product names of RoundupReady <registered trademark>, AgrisureGT <registered trademark>, and the like. Also, there are varieties of corn, soybean, cotton, and rapeseed which have acquired tolerance to glufosinate by gene recombinant technologies, and they are already commercially available with the product name of LibertyLink <registered trademark> and the like. In addition, the cotton that has acquired tolerance to bromoxynil by gene recombinant technologies is already commercially available with the product name of BXN.

The "horticultural plants" also include plants that have been enabled to synthesize, for example, selective toxins that are known to exist in *Bacillus*, by using gene recombinant technologies.

Examples of insecticidal toxins expressed in such gene recombinant plants include insecticidal proteins derived from *Bacillus cereus* and *Bacillus popilliae*; δ-endotoxins, such as Cry1Ab, Cry1Ac, Cry1F, Cry1Fa2, Cry2Ab, Cry3A, Cry3Bb1, and Cry9C, and insecticidal proteins, such as VIP1, VIP2, VIP3, and VIP3A, derived from *Bacillus thuringiensis*; insecticidal proteins derived from nematodes; toxins produced from organisms, such as scorpion toxins, spider toxins, bee toxins, and insect specific neurotoxins; filamentous fungus toxins; plant lectins; agglutinins; protease inhibitors, such as trypsin inhibitors, serine protease inhibitors, patatin, cystatin, and papain inhibitors; ribosome-inactivating proteins (RIPs), such as ricin, corn-RIP, abrin, saporin, and bryodin; steroid metabolic enzymes, such as 3-hydroxy steroid oxidase, ecdysteroid-UDP-glucosyltransferase, and cholesterol oxidase; ecdysone inhibitors; HMG-CoA reductases; ion channel inhibitors, such as sodium channel inhibitors and calcium channel inhibitors; juvenile hormone esterases; diuretic hormone receptors; stilbene synthases; bibenzyl synthases; chitinases; and glucanases.

The toxins expressed in such gene recombinant plants also include hybrid toxins, partially deleted toxins, and modified toxins of 6-endotoxin proteins, such as Cry1Ab, Cry1Ac, Cry1F, Cry1Fa2, Cry2Ab, Cry3A, Cry3Bb1, and Cry9C; and of insecticidal proteins, such as VIP1, VIP2, VIP3, and VIP3A. The hybrid toxins can be produced by using recombinant technologies as novel combinations of different domains of these proteins. As a partially deleted toxin, Cry1Ab, in which a portion of amino acid sequences is deleted, has been known. In a modified toxin, one or more amino acid(s) of a natural form of the toxin has(have) been substituted.

Examples of these toxins and recombinant plants that can synthesize these toxins are described in Patent Documents, such as EP-A-0374753, WO93/07278, WO95/34656, EP-A-0427529, EP-A-451878, and WO03/052073. The toxins contained in the recombinant plants can provide the plants with resistance particularly to Coleoptera pests, Diptera pests, and Lepidoptera pests.

The gene recombinant plants containing one or more insecticidal pest resistance gene(s) and expressing one or more toxin(s) have already been known, and some of them are commercially available. Examples of the gene recombinant plants include YieldGard <registered trademark> (a corn variety expressing Cry1Ab toxin), YieldGard Rootworm <registered trademark> (a corn variety expressing Cry3Bb1 toxin), YieldGard Plus <registered trademark> (a corn variety expressing Cry1Ab and Cry3Bb1 toxins), Herculex I<registered trademark> (a corn variety expressing Cry1Fa2 toxin and phosphinotricine N-acetyltransferase (PAT) for providing resistance to glufosinate), NuCOTN33B <registered trademark> (a cotton variety expressing Cry1Ac toxin), Bollgard I<registered trademark> (a cotton variety expressing Cry1Ac toxin), Bollgard II <registered trademark> (a cotton variety expressing Cry1Ac and Cry2Ab toxins), VIPCOT <registered trademark> (a cotton variety expressing VIP toxin), NewLeaf <registered trademark> (a potato variety expressing Cry3A toxin), NatureGard <registered trademark> Agrisure <registered trademark> GT Advantage (the GA21 glyphosate resistant trait), Agrisure <registered trademark> CB Advantage (the Btl 1 corn borer (CB) trait), and Protecta <registered trademark>.

These plants also include the plants that have been given abilities to produce anti-pathogenic substances having selective activities by using gene recombinant technologies.

Examples of the anti-pathogenic substances include PR proteins (PRPs, described in EP-A-0392225); ion channel inhibitors, such as sodium channel inhibitors and calcium channel inhibitors (KP1, KP4, KP6 toxins and the like produced by viruses have been known); stilbene synthases; bibenzyl synthases; chitinases; glucanases; and substances produced by microorganisms, such as peptide antibiotics, antibiotics having hetero rings, and protein factors responsible for resistance to plants diseases (referred to as plant disease resistance genes, and described in WO03/000906). These anti-pathogenic substances and gene recombinant plants producing thereof are described in EP-A-0392225, WO95/33818, EP-A-0353191, and the like.

These plants also include crops that have been provided with useful traits, such as traits of reformed oil and fat components or traits of enhanced amino acid components, by using gene recombinant technologies. Examples thereof include VISTIVE <registered trademark> (low linolenic soybeans in which linolenic contents are reduced) and high-lysine (hig hoil) corns (corns in which lysine or oil contents are increased).

These plants further include stacked varieties in which two or more useful traits such as classical herbicide traits; herbicide resistant genes; insecticidal pest resistant genes; anti-pathogenic substance producing genes; and traits of reformed oil and fat components or traits of enhanced amino acid components are combined.

Although the composition of the present invention can be used as a mixture comprising one or two selected from the first active ingredient compounds I and one or more selected from the second active ingredient compounds II exclusively, usually the composition is mixed with a suitable solid carrier or a liquid carrier, and if desired, a surfactant, a penetrant, a spreading agent, a thickener, an antifreezing agent, a binder, an anticaking agent, a disintegrant, an antifoaming agent, a preservative, a stabilizing agent, and the like are further added thereto, so that the composition can be provided for uses as a formulation of any dosage form, such as a soluble concentrate, an emulsifiable concentrate, a wettable powder, a water soluble powder, water dispersible granules, water soluble granules, a suspension concentrate, a concentrated emulsion, a suspoemulsion, a microemulsion, a dustable powder, granules, a tablet, and an emulsifiable gel. From the point of view of saving labor and improving safety, the formulation of any dosage form of above can be provided by including it in a water-soluble packaging body, such as a water-soluble capsule and a water-soluble film.

Examples of the solid carrier include natural minerals, such as quartz, calcite, meerschaum, dolomite, chalk, kaolinite, pyrophyllite, sericite, halloysite, metahalloysite, kibushi clay, potter's clay, pottery stone, zeeklite, allophane, silas, mica, talc, bentonite, activated white clay, acid clay, pumice stone, attapulgite, zeolite, and diatomaceous earth; burned natural mineral products, such as burned clay, pearlite, silas balloon, vermiculite, attapulgus clay, and burned diatomaceous earth; inorganic salts, such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate, and potassium chloride; sugars, such as glucose, fructose, sucrose, and lactose; polysaccharides, such as starch, powder cellulose, and dextrin; organic substances, such as urea, urea derivative, benzoic acid, and salts of benzoic acid; plants, such as wood powder, cork powder, corn rachises, walnut shells, and tobacco stems; fly ashes; white carbon (such as aqueous synthetic silica, anhydrous synthetic silica, and aqueous synthetic silicate); and fertilizers.

Examples of the liquid carrier include aromatic hydrocarbons, such as xylene, an alkyl ($C_9$, $C_{10}$, or the like) benzene, phenylxylyl ethane, and an alkyl ($C_1$, $C_3$, or the like) naphthalene; aliphatic hydrocarbons, such as a machine oil, normal paraffin, isoparaffin, and naphthene; a mixture of an aromatic hydrocarbon and an aliphatic hydrocarbon, such as kerosene; alcohols, such as ethanol, isopropanol (2-propanol), cyclohexanol, phenoxyethanol, and benzyl alcohol; polyalcohols, such as ethylene glycol, propylene glycol, diethylene glycol, hexylene glycol, polyethylene glycols, and polypropylene glycols; ethers, such as propyl cellosolve, butyl cellosolve, phenyl cellosolve, propylene glycol monomethyl ether, propylene glycol monoethyl ether, propylene glycol monopropyl ether, propylene glycol monobutyl ether, and propylene glycol monophenyl ether; ketones, such as acetophenone, cyclohexanone, and γ-butyrolactone; esters, such as fatty acid methyl esters, succinic acid dialkyl esters, glutamic acid dialkyl esters, adipic acid dialkyl esters, and phthalic acid dialkyl esters; acid amides, such as a N-alkyl ($C_1$, $C_8$, $C_{12}$, or the like) pyrrolidone; fats and oils, such as soybean oil, flaxseed oil, canola oil, coconut oil, cottonseed oil, and castor oil; dimethyl sulfoxide; and water.

These solid and liquid carriers may be used alone, or two or more of them may be used in combination.

Examples of the surfactant include nonionic surfactants, such as a polyoxyethylene alkyl ether, a polyoxyethylene alkyl (mono or di)phenyl ether, a polyoxyethylene (mono, di, or tri)styrylphenyl ether, a polyoxyethylene-polyoxypropylene block copolymer, a polyoxyethylene fatty acid (mono or di)ester, a sorbitan fatty acid ester, a polyoxyethylene sorbitan fatty acid ester, a castor oil ethylene oxide adduct, acetylene glycol, an acetylene alcohol, an ethylene oxide adduct of acetylene glycol, an ethylene oxide adduct of an acetylene alcohol, and an alkyl glycoside; anionic surfactants, such as an alkyl sulfuric acid ester salt, an alkyl benzenesulfonate, lignin sulfonate, an alkyl sulfosuccinate, naphthalenesulfonate, an alkyl naphthalenesulfonate, a salt of a formalin condensate of naphthalenesulfonate, a salt of a formalin condensate of an alkyl naphthalenesulfonate; a polyoxyethylene alkyl ether sulfuric acid or phosphoric acid ester salt, a polyoxyethylene (mono or di)alkyl phenyl ether sulfuric acid or phosphoric acid ester salt, a polyoxyethylene (mono, di, or tri)styrylphenyl ether sulfuric acid or phosphoric acid ester salt, a polycarboxylate (for example, a polyacrylate, a polymaleate, a copolymer of maleic acid and olefin, and the like), and polystyrene sulfonate; cationic surfactants, such as an alkylamine salt and an alkyl quaternary ammonium salt; amphoteric surfactants, such as amino acid surfactants and betaine surfactants; silicone-based surfactants; and fluorine-based surfactants. Although the content of the surfactant is not particularly limited, it is preferably within a range of 0.05 part by weight to 20 parts by weight with respect to 100 parts by weight of the formulation of the present invention. These surfactants may be used alone, or two or more of them may be used in combination.

Next, mixing examples of formulations in which the composition of the present invention is used will be shown. However, mixing examples of the present invention are not limited thereto. Note that, in the mixing examples below, "part(s)" refers to part(s) by weight, and "active ingredient compound" is a collective term referring to the first active ingredient compound I and the second active ingredient compound II of the composition of the present invention.

[Wettable Powder]

| | |
|---|---|
| Active ingredient compound | 0.1 part to 80 parts |
| Solid carrier | 5 parts to 98.9 parts |
| Surfactant | 1 part to 10 parts |
| Others | 0 part to 5 parts |

Examples of "others" include an anticaking agent and a stabilizing agent.

[Emulsifiable Concentrate]

| | |
|---|---|
| Active ingredient compound | 0.1 part to 30 parts |
| Liquid carrier | 45 parts to 95 parts |
| Surfactant | 4.9 parts to 15 parts |
| Others | 0 part to 10 parts |

Examples of "others" include a spreading agent and a stabilizing agent.

[Suspension Concentrate]

| Active ingredient compound | 0.1 part to 70 parts |
|---|---|
| Liquid carrier | 15 parts to 98.89 parts |
| Surfactant | 1 part to 12 parts |
| Others | 0.01 part to 30 parts |

Examples of "others" include an antifreezing agent and a thickener.

[Water Dispersible Granule]

| Active ingredient compound | 0.1 part to 90 parts |
|---|---|
| Solid carrier | 0 part to 98.9 parts |
| Surfactant | 1 part to 20 parts |
| Others | 0 part to 10 parts |

Examples of "others" include a binder and a stabilizing agent.

[Soluble Concentrate]

| Active ingredient compound | 0.01 part to 70 parts |
|---|---|
| Liquid carrier | 20 parts to 99.99 parts |
| Others | 0 part to 10 parts |

Examples of "others" include an antifreezing agent and a spreading agent.

[Granule]

| Active ingredient compound | 0.01 part to 80 parts |
|---|---|
| Solid carrier | 10 parts to 99.99 parts |
| Others | 0 part to 10 parts |

Examples of "others" include a binder and a stabilizing agent.

[Dustable Powder]

| Active ingredient compound | 0.01 part to 30 parts |
|---|---|
| Solid carrier | 65 parts to 99.99 parts |
| Others | 0 part to 5 parts |

Examples of "others" include an anti drift agent and a stabilizing agent.

Next, specific examples of the agrochemical formulation containing the composition of the present invention as the active ingredient will be shown; however, the present invention is not limited thereto.

Note that, "part(s)" in the mixing examples below refers to part(s) by weight.

[Mixing Example 1] Wettable Powder

| Compound (1) | 10 parts |
|---|---|
| Compound No. mu | 10 parts |
| Pyrophyllite | 76 parts |
| SORPOL 5039 (a mixture of a nonionic surfactant and an anionic surfactant: the name of the product of TOHO Chemical Industry Co., Ltd.) | 2 parts |
| Carplex #80D (synthetic hydrous silicate: the name of the product of Shionogi & Co., Ltd.) | 2 parts |

These materials are uniformly mixed and pulverized to prepare a wettable powder.

[Mixing Example 2] Emulsifiable Concentrate

| Compound (1) | 3 parts |
|---|---|
| Compound No. nr | 2 parts |
| Xylene | 75 parts |
| N-methylpyrrolidone | 15 parts |
| SORPOL 2680 (a mixture of a nonionic surfactant and an anionic surfactant: the name of the product of TOHO Chemical Industry Co., Ltd.) | 5 parts |

These materials are uniformly mixed to prepare an emulsifiable concentrate.

[Mixing Example 3] Suspension Concentrate

| Compound (1) | 15 parts |
|---|---|
| Compound No. no | 10 parts |
| AGRISOL S-710 (nonionic surfactant: the name of the product of Kao Corporation) | 10 parts |
| Lunox 1000C (anionic surfactant: the name of the product of TOHO Chemical Industry Co., Ltd.) | 0.5 part |
| Xanthan gum | 0.2 part |
| Water | 64.3 parts |

These materials are uniformly mixed, and then wet milled to prepare a suspension concentrate.

[Mixing Example 4] Water Dispersible Granule

| Compound (1) | 40 parts |
|---|---|
| Compound No. ny | 35 parts |
| HITENOL NE-15 (anionic surfactant: the name of the product of DKS Co. Ltd.) | 5 parts |
| VANILLEX N (anionic surfactant: the name of the product of Nippon Paper Industries Co., Ltd.) | 10 parts |
| Carplex #80D (synthetic hydrous silicate: the name of the product of Shionogi & Co., Ltd.) | 10 parts |

These materials are uniformly mixed and pulverized. After a small amount of water is added thereto, the mixture is stirred. Then, the mixture is granulated with an extrusion granulator, and is dried to obtain water dispersible granules.

[Mixing Example 5] Granule

| Compound (1) | 3 parts |
|---|---|
| Compound No. nx | 2 parts |
| Bentonite | 50 parts |
| Talc | 45 parts |

These materials are uniformly mixed and pulverized. After a small amount of water is added thereto, the mixture is stirred. Then, the mixture is granulated with an extrusion granulator, and is dried to obtain granules.

[Mixing Example 6] Dustable Powder

| Compound (1) | 2 parts |
| Compound No. nb | 1 parts |
| Carplex #80D | 0.5 part |
| (white carbon: the name of the product of Shionogi & Co., Ltd.) | |
| Kaolinite | 95 parts |
| Diisopropyl phosphate | 1.5 parts |

These materials are uniformly mixed and pulverized to prepare a dustable powder.

At the time of use, the wettable powder, emulsifiable concentrate, flowable agent, and water dispersible granules are diluted to 50 to 20,000-fold with water in order to spray 0.005 kg to 50 kg of the active ingredient per 1 hectare (ha).

In the present invention, the composition of the present invention, which contains the first active ingredient compound I and the second active ingredient compound II, can be made as a formulation for uses, as described above. However, a chemical containing the first active ingredient compound I or the second active ingredient compound II as an active ingredient can be prepared separately, and then these chemicals can be used at the same time or at different times that are close to each other, in order to obtain excellent synergistic control effects. Note that, when these chemicals are used at different times that are close to each other, the second chemical is preferably sprayed after the first sprayed chemical is sufficiently dried. However, it may vary depending on control methods, diseases to be controlled, and the like.

EXAMPLES

Hereinafter, a method for manufacturing Compound (1) and Compound (2) used in the composition of the present invention will be specifically explained.

[Synthesis Example 1] Manufacture of Compound (1)

In a 100 ml pressure reaction vessel, 3.00 g (6.62 mmol) of 3-(4-bromo-3-methylphenyl)-5-(3,5-dichlorophenyl)-5-trifluoromethyl-4,5-dihydroisoxazole (2-1) that was synthesized according to the method described in WO2010/005048, 1.24 g (7.95 mmol) of 2-amino-N-(2,2,2-trifluoroethyl)acetamide, 1.1 g (7.95 mmol) of potassium carbonate, 41.0 mg (0.099 mmol) of 1,3-bis(diphenylphosphino)propane, 0.14 g (0.033 mmol) of 5% by mass palladium-carbon (50% aqueous), and 30 ml of 1,2-dimethoxyethane were placed. After the reaction vessel was purged with nitrogen, then with carbon monoxide, the reaction vessel was filled with the carbon monoxide at 1.0 MPa. The temperature was raised to 105° C., and a reaction was performed for 5 hours as stirred at the same temperature. During the reaction, the pressure inside was increased to 1.3 MPa at most. After that, the reaction vessel was cooled to room temperature, the pressure inside of the vessel was reduced to atmospheric pressure, and the reaction vessel was purged with nitrogen. Insoluble matter in the reaction solution was filtered off by celite filtration, and the celite was washed with ethyl acetate and water. The obtained filtrate was made to be acidic by adding concentrated hydrochloric acid. After an aqueous phase was separated, an organic phase was washed with saline. The organic phase was dried with anhydrous magnesium sulfate. After filtering off, a solvent was removed by vacuum distillation. The obtained residue was crystallized with ethyl acetate/hexane=3/18 (ml) to obtain 2.54 g (4.57 mmol) of the target material as a light yellow solid.

[Synthesis Example 2] Manufacture of Compound (2)

Synthesis Example 2-1: Synthesis of 4-[5-(3,5-dichlorophenyl)-5-trifluoromethyl-4,5-dihydroisoxazole-3-yl]-2-methylbenzamide To a reaction vessel equipped with a Dean-Stark apparatus whose trap was filled with toluene, 10.0 g of 4-acetyl-2-methylbenzamide, 143.7 g of toluene, and 1.9 g of water were added in this order, and the mixture was heated at 85° C. as stirred for 1 hour. After the stirring was completed, 13.9 g of 3',5'-dichloro-2,2,2-trifluoromethyl acetophenone and 2.8 g of a 5% by weight tetrabutyl ammonium hydroxide aqueous solution were added thereto, and the mixture was heated at 85° C. as stirred for 1 hour. After the stirring was completed, the reaction mixture was continued to be stirred at 65° C. for 3 hours. After the stirring was completed, the pressure was reduced to 20 kPa, and the mixture was refluxed for 12 hours to be azeotropically dehydrated. After the stirring was completed, the mixture was cooled to 0° C., and 2.5 g of 1,8-diazabicyclo[5,4,0]-7-undecene, 9.5 g of 1,1,3,3-tetramethylguanidine, and 18.3 g of a 25% by weight hydroxyamine aqueous solution were added thereto. After the addition was completed, the reaction mixture was stirred for 21 hours at the same temperature. After the stirring was completed, 8.0 g of a 20% by weight hydrochloric acid aqueous solution and 63.1 g of 2-propanol were added thereto. The obtained reaction mixture was washed three times with 53.4 g of water, and then 50.4 g of the solvent was removed by vacuum distillation. 28.8 g of toluene was further added thereto, and the mixture was heated to 100° C. to dissolve slurry, and then cooled to 0° C. to be crystallized. After the obtained slurry was filtrated, the obtained crystal was washed with 19.2 g of toluene that was cooled to 0° C. The obtained solid was vacuum-dried to obtain 16.7 g of the target material. The obtained solid was analyzed by an internal reference analysis method using HPLC, and the result showed that the purity was 98.3%.

The conditions of the analysis using HPLC are shown below.

Column: Inertsil Ph-3 50 mm 4.6 mm φ 3 μm (manufactured by GL Sciences Inc.)
Flow rate: 1 mL/min
Eluent: acetonitrile/water/acetic acid=800/1,200/1.2 (volume ratio)
Detection: UV 220 nm
Internal standard material: 4-t-butylbiphenyl Synthesis Example 2-2: Synthesis of Compound (2)

2.00 g of 4-[5-(3,5-dichlorophenyl)-5-trifluoromethyl-4,5-dihydroisoxazole-3-yl]-2-methylbenzamide that was obtained in Synthesis Example 2-1, 4.26 g of ortho formic acid triethyl, and 10 ml of a 0.60 g methoxyamine hydrochloride toluene solution were stirred at 35° C. for 24 hours. After the stirring was completed, 10 ml of toluene was added to the reaction solution. After the addition was completed, the reaction solution was heated to 60° C. to 65° C., and washed with water (4 ml×3 times). 10 ml of toluene was removed from the obtained toluene solution by vacuum distillation. After the removal by vacuum distillation, the toluene solution was cooled from about 70° C. at a rate of about 20° C./hour. After crystals were generated in the toluene solution, the solution was stirred at 0° C. to 5° C. for 3 hours. After the stirring was completed, the deposited crystals were separated by vacuum filtration, and the obtained crystals were vacuum-dried to obtain 1.92 g of the target material as white crystals.

Test Example

Next, the usefulness of the present invention will be specifically explained in the Efficacy Test Examples below. However, the present invention is not limited thereto.

[Test Example 1] Efficacy Test for Common Cutworm

Each of Compound (1) or Compound (2) and the compounds listed in Table 1 was formulated into a 10% emulsifiable concentrate (some compound was formulated into a 25% wettable powder). The formulations were diluted with water containing a spreading agent to prepare chemical solutions of given concentrations. Cabbage leaves were dipped in the chemical solutions for 10 seconds. The dipped cabbage leaves were transferred on filter papers placed in 7 cm petri dishes with one leaf per one petri dish, and the leaves were air dried. After the air drying was completed, the seven third instar larvae of common cutworms were placed in each petri dish and then the petri dishes were placed in an incubator at 25° C. Six days after the treatment, the numbers of dead larvae were checked, and the percentages of dead insects were calculated according to the calculating equation below. Note that the tests were conducted in duplicate.

The percentage of dead insects (%)=the number of dead insects/the number of tested insects×100

To each concentration of chemical solutions, the synergistic effect was calculated from the percentage of dead insects by using Colby's method (Colby S. R. 1976, Weeds 15, 20-22). The calculation method was as follows.

$E=X+Y-XY/100$

X: an observed value at an x concentration of Chemical A (the percentage of dead insects)
Y: an observed value at a y concentration of Chemical B (the percentage of dead insects)
E: the percentage of dead insects expected at the time of a mixed treatment with Chemical A and Chemical B.

The obtained results were analyzed as follows. If the observed value was larger than the expected value, there was a synergistic effect; if the expected value was larger than the observed value, there was an antagonist effect; and if the observed value and the expected value were same, there was an additive effect. The combinations that showed synergistic effects are listed in Tables 3 to 8 below.

TABLE 3

| Active ingredient | Concentration (ppm) | Percentage of Dead Insect (%) Observed Value | Percentage of Dead Insect (%) Expected Value |
|---|---|---|---|
| Compound (1) | 0.017 | 28.6 | |
| Compound (2) | 0.017 | 35.7 | |
| Compound aa | 0.083 | 21.4 | |
| Compound ar | 0.5 | 35.7 | |
| Compound (1) + Compound aa | 0.017 + 0.083 | 85.7 | 43.9 |
| Compound (1) + Compound ar | 0.017 + 0.5 | 78.6 | 54.1 |
| Compound (2) + Compound aa | 0.017 + 0.083 | 85.7 | 49.5 |
| Compound (2) + Compound ar | 0.017 + 0.5 | 71.4 | 58.7 |
| Non-treated | 0 | 0 | |

TABLE 4

| Active ingredient | Concentration (ppm) | Percentage of Dead Insect (%) Observed Value | Percentage of Dead Insect (%) Expected Value |
|---|---|---|---|
| Compound (2) | 0.025 | 35.7 | |
| Compound em | 32 | 60.0 | |
| Compound (2) + Compound em | 0.025 + 32 | 92.9 | 74.3 |
| Non-treated | 0 | 0 | |

TABLE 5

| Active ingredient | Concentration (ppm) | Percentage of Dead Insect (%) Observed Value | Percentage of Dead Insect (%) Expected Value |
|---|---|---|---|
| Compound (2) | 0.025 | 35.7 | |
| Compound el | 4.4 | 78.6 | |
| Compound (2) + Compound el | 0.025 + 32 | 100 | 86.2 |
| Non-treated | 0 | 0 | |

TABLE 6

| Active ingredient | Concentration (ppm) | Percentage of Dead Insect (%) Observed Value | Percentage of Dead Insect (%) Expected Value |
|---|---|---|---|
| Compound (2) | 0.025 | 35.7 | |
| Compound dc | 1.7 | 53.8 | |
| Compound (2) + Compound dc | 0.025 + 1.7 | 83.3 | 70.3 |
| Non-treated | 0 | 0 | |

TABLE 7

| Active ingredient | Concentration (ppm) | Percentage of Dead Insect (%) Observed Value | Percentage of Dead Insect (%) Expected Value |
|---|---|---|---|
| Compound (2) | 0.005 | 14.3 | |
| Compound am | 0.17 | 7.7 | |
| Compound (2) + Compound am | 0.005 + 0.17 | 61.5 | 20.9 |
| Non-treated | 0 | 0 | |

TABLE 8

| Active ingredient | Concentration (ppm) | Percentage of Dead Insect (%) Observed Value | Percentage of Dead Insect (%) Expected Value |
|---|---|---|---|
| Compound (2) | 0.005 | 14.3 | |
| Compound ey | 1.7 | 64.3 | |
| Compound (2) + Compound ey | 0.005 + 0.17 | 84.6 | 69.4 |
| Non-treated | 0 | 0 | |

[Test Example 2] Efficacy Test for Cotton Bollworm

Each of Compound (1) or Compound (2) and the compounds listed in Table 1 was formulated into a 10% emulsifiable concentrate (some compound was formulated into a 25% wettable powder). The formulations were diluted with water containing a spreading agent to prepare chemical solutions of given concentrations. Cabbage leaves were dipped in the chemical solutions for 10 seconds. The dipped cabbage leaves were transferred on filter papers placed in 7 cm petri dishes with one leaf per one petri dish, and the leaves were air dried. After the air drying was completed, the seven fourth instar larvae of cotton bollworms were placed in each petri dish, and then, the petri dishes were placed in an incubator at 25° C. Six days after the treatment, the numbers of dead larvae were checked, and the percentages of dead insects were calculated according to the calculating equation below. Note that the tests were conducted in duplicate.

The percentage of dead insects (%)=the number of dead insects/the number of tested insects×100

To each concentration of chemical solutions, the synergistic effect was calculated from the percentage of dead insects by using Colby's method (Colby S. R. 1976, Weeds 15, 20-22). The calculation method was as follows.

$E=X+Y-XY/100$

X: an observed value at an x concentration of Chemical A (the percentage of dead insects)
Y: an observed value at a y concentration of Chemical B (the percentage of dead insects)
E: the percentage of dead insects expected at the time of a mixed treatment with Chemical A and Chemical B.

The obtained results were analyzed as follows. If the observed value was larger than the expected value, there was a synergistic effect; if the expected value was larger than the observed value, there was an antagonist effect; and if the observed value and the expected value were same, there was an additive effect. The combinations that showed synergistic effects are listed in Table 9 below.

TABLE 9

| Active ingredient | Concentration (ppm) | Percentage of Dead Insect (%) Observed Value | Percentage of Dead Insect (%) Expected Value |
|---|---|---|---|
| Compound (1) | 0.125 | 28.6 | |
| Compound (2) | 0.125 | 35.7 | |
| Compound al | 0.25 | 42.9 | |
| Compound ca | 0.025 | 35.7 | |
| Compound (1) + Compound al | 0.125 + 0.25 | 92.9 | 59.2 |
| Compound (1) + Compound ca | 0.125 + 0.025 | 85.7 | 54.1 |
| Compound (2) + Compound al | 0.125 + 0.25 | 85.7 | 63.3 |
| Compound (2) + Compound ca | 0.125 + 0.025 | 100 | 58.7 |
| Non-treated | 0 | 0 | |

[Test Example 3] Efficacy Test for Sweetpotato Whitefly Biotype B

Each of Compound (1) or Compound (2) and the compounds listed in Table 1 was formulated into a 10% emulsifiable concentrate. The formulations were diluted with water to prepare chemical solutions of given concentrations. A styrol cup (having the diameter of the lid of 7.5 cm, and the height of 4 cm) was filled with tap water, and a lid having a hole in its center was placed on the styrol cup, and a filter paper was placed on the lid to absorb tap water. An absorbent cotton (5 cm×5 cm) wetted with tap water was placed on the filter paper, and a leaf disk (having the diameter of 3 cm) made of a common bean leaf was placed on the absorbent cotton. Each of the test containers was treated with a spray solution as was uniformly sprayed by using a spraying apparatus (2.5 ml/cup). The 20 sweetpotato whitefly adult insects were placed on the leaf disk, and a mesh lid was placed over the container to prevent escape of the insects. Examinations were conducted 5 days after spraying, and the percentages of dead insects were calculated according to the calculating equation below. Note that the tests were conducted in duplicate.

The percentage of dead insects (%)=the number of dead insects/the number of tested insects×100

To each concentration of chemical solutions, the synergistic effect was calculated from the percentage of dead insects by using Colby's method (Colby S. R. 1976, Weeds 15, 20-22). The calculation method was as follows.

$E=X+Y-XY/100$

X: an observed value at an x concentration of Chemical A (the percentage of dead insects)
Y: an observed value at a y concentration of Chemical B (the percentage of dead insects)
E: the percentage of dead insects expected at the time of a mixed treatment with Chemical A and Chemical B.

The obtained results were analyzed as follows. If the observed value was larger than the expected value, there was a synergistic effect; if the expected value was larger than the observed value, there was an antagonist effect; and if the observed value and the expected value were same, there was an additive effect. The combinations that showed synergistic effects are listed in Table 10 below.

TABLE 10

| Active ingredient | Concentration (ppm) | Percentage of Dead Insect (%) Observed Value | Percentage of Dead Insect (%) Expected Value |
|---|---|---|---|
| Compound (2) | 5 | 36.6 | |
| Compound ci | 25 | 40.5 | |
| Compound (2) + Compound ci | 5 + 25 | 82.1 | 62.3 |
| Non-treated | 0 | 15.8 | |

[Test Example 4] Efficacy Test for Melon Thrips Female Adult Insect

Each of Compound (1) or Compound (2) and the compounds listed in Table 1 was formulated into a 10% emulsifiable concentrate. The formulations were diluted with water to prepare chemical solutions of given concentrations. A styrol cup (having the diameter of the lid of 7.5 cm, and the height of 4 cm) was filled with tap water, and a lid having a hole in its center was placed on the styrol cup, and a filter paper was placed on the lid to absorb tap water. An absorbent cotton (5 cm×5 cm) wetted with tap water was placed on the filter paper, and a leaf disk (having the diameter of 1.7 cm) made of a cucumber leaf was placed on the absorbent cotton. The ten melon thrips female adult insects were placed on the leaf disk. Each of the test containers was treated with a spray solution as was uniformly sprayed by using a spraying apparatus (2.5 ml/cup). Examinations were conducted 2 days after spraying, and the percentages of dead insects were calculated according to the calculating equation below. Note that the tests were conducted in duplicate.

The percentage of dead insects (%)=the number of dead insects/the number of tested insects×100

To each concentration of chemical solutions, the synergistic effect was calculated from the percentage of dead insects by using Colby's method (Colby S. R. 1976, Weeds 15, 20-22). The calculation method was as follows.

$E=X+Y-XY/100$

X: an observed value at an x concentration of Chemical A (the percentage of dead insects)
Y: an observed value at a y concentration of Chemical B (the percentage of dead insects)
E: the percentage of dead insects expected at the time of a mixed treatment with Chemical A and Chemical B.

The obtained results were analyzed as follows. If the observed value was larger than the expected value, there was a synergistic effect; if the expected value was larger than the observed value, there was an antagonist effect; and if the observed value and the expected value were same, there was an additive effect. The combinations that showed synergistic effects are listed in Table 11 below.

TABLE 11

| Active ingredient | Concentration (ppm) | Percentage of Dead Insect (%) Observed Value | Percentage of Dead Insect (%) Expected Value |
| --- | --- | --- | --- |
| Compound (2) | 5 | 42.1 | |
| Compound bx | 2.5 | 52.6 | |
| Compound (2) + Compound bx | 5 + 2.5 | 84.2 | 72.6 |
| Non-treated | 0 | 15 | |

[Test Example 5] Efficacy Test for Western Flower *Thrips* Larva

A styrol cup (having the diameter of the lid of 7.5 cm, and the height of 4 cm) was filled with tap water, and a lid having a hole in its center was placed on the styrol cup, and a leaf disk (having the diameter of 1.7 cm) made of a common bean leaf was placed on the lid. Suitable amounts of eggs of Western flower thrips were placed on the leaf disk, and were controlled in a thermostatic chamber for 24 hours to be hatched. Each of Compound (1) or Compound (2) and the compounds listed in Table 1 was formulated into a 10% emulsifiable concentrate. The formulations were diluted with water to prepare chemical solutions of given concentrations. Each of the test containers was treated with a spray solution as was uniformly sprayed by using a spraying apparatus (2.5 ml/cup). Examinations were conducted 1 day after spraying, and the percentages of dead insects were calculated according to the calculating equation below. Note that the tests were conducted in duplicate.

The percentage of dead insects (%)=the number of dead insects/the number of tested insects×100

To each concentration of chemical solutions, the synergistic effect was calculated from the percentage of dead insects by using Colby's method (Colby S. R. 1976, Weeds 15, 20-22). The calculation method was as follows.

$E=X+Y-XY/100$

X: an observed value at an x concentration of Chemical A (the percentage of dead insects)
Y: an observed value at a y concentration of Chemical B (the percentage of dead insects)
E: the percentage of dead insects expected at the time of a mixed treatment with Chemical A and Chemical B.

The obtained results were analyzed as follows. If the observed value was larger than the expected value, there was a synergistic effect; if the expected value was larger than the observed value, there was an antagonist effect; and if the observed value and the expected value were same, there was an additive effect. The combinations that showed synergistic effects are listed in Table 12 below.

TABLE 12

| Active ingredient | Concentration (ppm) | Percentage of Dead Insect (%) Observed Value | Percentage of Dead Insect (%) Expected Value |
| --- | --- | --- | --- |
| Compound (2) | 1 | 29.5 | |
| Compound q | 20 | 8.5 | |
| Compound ce | 20 | 27.2 | |
| Compound (2) + Compound q | 1 + 20 | 56.6 | 35.4 |
| Compound (2) + Compound ce | 1 + 20 | 72.0 | 48.7 |
| Non-treated | 0 | 8.0 | |

[Reference Example 1] Efficacy Test for *Varroa* Mite

The Compound (1) or Compound (2) was adjusted to a given concentration with acetone. After the adjustment, 300 μl of each of the prepared solutions was poured into a 20 ml screw bottle. The solvent was volatilized as the inner surface of the bottle was uniformly coated with the solution, and then the bottle was stored in a cool and dark place overnight. To obtain *varroa* mites, a blood comb was taken out from a beehive of honey bees on the day before placing of mites, and pupae having *varroa* mites were taken and placed in a petri dish. The petri dish was stored in an incubator at 34° C. overnight under the total darkness condition, and then only surviving *varroa* mites were collected. The collected *varroa* mites were placed in each of the screw bottles that were treated with the above-described chemicals, and the screw bottles were closed with caps. After three hours, the pupae of honey bees were placed in the screw bottles; the screw bottles were closed with caps again, and were stored in an incubator at 34° C. under the total darkness condition. The number of dead insects 24 hours after placing was checked, and the percentages of dead insects were calculated according to the calculating equation below. The results are shown in Table 13. Note that the tests were conducted in quadruplicate of three in one plot.

The percentage of dead insects (%)=the number of dead insects/the number of tested insects×100

TABLE 13

| Active ingredient | Concentration (μg/tube) | Percentage of Dead Insect (%) |
|---|---|---|
| Compound No. (1) | 100 | 100 |
| Compound No. (2) | 100 | 100 |
| Non-treated | 0 | 0 |

INDUSTRIAL APPLICABILITY

The composition of the present invention and the method of the present invention can be used for controlling various pests.

The invention claimed is:

1. An insecticidal, miticidal, nematicidal, molluscicidal, microbicidal, or bactericidal composition comprising at least two types of active compounds with amounts that are synergistically active, wherein the two types of active compounds include:

1) an active compound I containing (Z)-4-[5-(3,5-dichlorophenyl)-5-trifluoromethyl-4,5-dihydroisoxazole-3-yl]-N-(methoxyiminomethyl)-2-methylbenzamide; and 2) one or more active compound(s) II selected from the group consisting of cyclaniliprole, tetraniliprole, flupyradifurone, and flometoquin.

2. A method for controlling pests wherein a treatment is conducted with an active compound I containing (Z)-4-[5-(3,5-dichlorophenyl)-5-trifluoromethyl-4,5-dihydroisoxazole-3-yl]-N-(methoxyiminomethyl)-2-methylbenzamide and one or more active compound(s) II selected from the group consisting of cyclaniliprole, tetraniliprole, flupyradifurone, and flometoquin.

* * * * *